United States Patent
Woods et al.

(10) Patent No.: US 8,323,958 B2
(45) Date of Patent: Dec. 4, 2012

(54) CLOSED PHOTOBIOREACTOR SYSTEM FOR CONTINUED DAILY IN SITU PRODUCTION OF ETHANOL FROM GENETICALLY ENHANCED PHOTOSYNTHETIC ORGANISMS WITH MEANS FOR SEPARATION AND REMOVAL OF ETHANOL

(75) Inventors: R. Paul Woods, Naples, FL (US); Edward Legere, Lake Worth, FL (US); Benjamin Moll, Davis, CA (US); Edwin Malkiel, Baltimore, MD (US)

(73) Assignee: Algenol Biofuels Switzerland GmbH, Bonita Springs, FL (US)

( * ) Notice: Subject to any disclaimer, the term of this patent is extended or adjusted under 35 U.S.C. 154(b) by 565 days.

(21) Appl. No.: 12/387,911

(22) Filed: May 8, 2009

(65) Prior Publication Data

US 2010/0068801 A1    Mar. 18, 2010

Related U.S. Application Data

(63) Continuation-in-part of application No. 11/929,503, filed on Oct. 30, 2007, now Pat. No. 7,682,821.

(60) Provisional application No. 60/864,091, filed on Nov. 2, 2006.

(51) Int. Cl.
*C12M 1/00* (2006.01)
*C12M 3/00* (2006.01)

(52) U.S. Cl. .......... 435/292.1; 435/262; 435/290.4; 435/296.1; 435/303.1; 435/307.1; 47/1.4

(58) Field of Classification Search .... 435/289.1–309.4, 435/262, 290.1–290.4, 292.1, 298.1, 303.1, 435/307.1
See application file for complete search history.

(56) References Cited

U.S. PATENT DOCUMENTS

| | | | | | |
|---|---|---|---|---|---|
| 4,337,315 | A | * | 6/1982 | Fukushima et al. | 435/296.1 |
| 4,455,374 | A | | 6/1984 | Schwartz | |
| 5,206,173 | A | * | 4/1993 | Finn | 435/290.1 |
| 5,958,761 | A | | 9/1999 | Yogev et al. | |
| 6,083,740 | A | | 7/2000 | Kodo et al. | |
| 6,405,777 | B1 | * | 6/2002 | Lebbad | 156/391 |
| 6,699,696 | B2 | | 3/2004 | Woods et al. | |
| 7,135,332 | B2 | * | 11/2006 | Ouellette | 435/290.1 |
| 7,682,821 | B2 | | 3/2010 | Woods et al. | |
| 7,980,024 | B2 | | 7/2011 | Berzin et al. | |
| 2003/0170409 | A1 | * | 9/2003 | Porter et al. | 428/34.9 |
| 2005/0260553 | A1 | | 11/2005 | Berzin | |
| 2008/0009055 | A1 | * | 1/2008 | Lewnard | 435/262 |

(Continued)

FOREIGN PATENT DOCUMENTS

WO    WO 81/03182    11/1981

(Continued)

OTHER PUBLICATIONS

Meukam, P., et al, Chemical engineering and processing, 2004, 43, 1569-1577.*

(Continued)

*Primary Examiner* — William H Beisner
*Assistant Examiner* — Shanta G Doe
(74) *Attorney, Agent, or Firm* — Lawrence B. Ebert; David J. Lorenz

(57) ABSTRACT

The invention provides a device for growing genetically enhanced aquatic photoautotrophic organisms in a stable culture, causing said organisms to produce ethanol, and then separating, collecting, and removing the ethanol in situ.

3 Claims, 24 Drawing Sheets

U.S. PATENT DOCUMENTS

2009/0130706 A1* 5/2009 Berzin et al. .................. 435/41

FOREIGN PATENT DOCUMENTS

| WO | WO 2007/084477 | | 7/2007 |
|----|----------------|---|--------|
| WO | WO 2008033573 | | 3/2008 |
| WO | WO2008033573 | * | 3/2008 |
| WO | WO 2008/051865 | | 5/2008 |
| WO | WO 2008/055190 | | 5/2008 |

OTHER PUBLICATIONS

Murugavel et al., "Progresses in Improving the Effectiveness of the Single Basin Passive Solar Still," Desalination 220:677-686 (2008).

Namprakai et al., "Ethyl Alcohol Distillation in a Basin Solar Still," Renewable Energy 11:169-175 (1997).

Gudin et al., "Cell Fragility—The Key Problem of Microalgae Mass Production in Closed Photobioreactors," Bioresource Technology 38:145-151 (1991).

Janssen et al. "Scale-up Aspects of Photobioreactors: Effects of Mixing-Induced Light/Dark Cycles," Jour. Appl. Phycol. 12:225-237 (2000).

Javanmardian et al., "High Density Photoautotrophic Algal Cultures: Design, Construction, and Operation of a Novel Photobioreactor System," Biotechnology & Bioengineering 38:1182-1189 (1991).

Ogbonna et al., "Industrial-Size Photobioreactors," Chemtech 27:43-49 (1997).

Lee et al., "High-Density Algal Photobioreactors using Light-Emitting Diodes," Biotechnology and Bioengineering 44:1161-1167 (1994).

Hu et al., "Ultrahigh-Cell-Density Culture of Marine Green Alga *Chlorococcum littorale* in a Flat-Plate Photobioreactor," Applied Microbiol. Biotech. 49:655-662 (1998).

Fernandez et al., "Airlift-Driven External-Loop Tubular Photobioreactors for Outdoor Production of Microalgae: Assessment of Design and Performance," Chemical Engineering Science 56:2721-2732 (2001).

Ugwu et al., "Photobioreactors for Mass Cultivation of Algae," Bioresource Technology 99:4021-4028 (2008).

U.S. Appl. No. 60/864,091, filed Nov. 2, 2006.

Office Action for U.S. Appl. No. 11/929,503, dated Jul. 29, 2008.

Declaration of inventor under C.F.R. § 1.132 for U.S. Appl. No. 11/929,503, dated Nov. 25, 2008.

Amendment and Response to Office Action for U.S. Appl. No. 11/929,503, dated Nov. 28, 2008.

Office Action for U.S. Appl. No. 11/929,503, dated Feb. 25, 2009.

Examiner interview summary record for U.S. Appl. No. 11/929,503, dated Apr. 15, 2009.

Amendment and Response to Office Action for U.S. Appl. No. 11/929,503, dated Apr. 22, 2009.

Office Action for U.S. Appl. No. 11/929,503, dated May 5, 2009.

Examiner interview summary record for U.S. Appl. No. 11/929,503, dated Jul. 31, 2009.

Declaration of inventor under C.F.R. § 1.132 for U.S. Appl. No. 11/929,503, dated Aug. 2, 2009.

Amendment and Response to Office Action for U.S. Appl. No. 11/929,503, dated Aug. 5, 2009.

Office Action for U.S. Appl. No. 11/929,503, dated Oct. 23, 2009.

Amendment and Response to Office Action for U.S. Appl. No. 11/929,503, dated Nov. 12, 2009.

Supplemental Response to Office Action for U.S. Appl. No. 11/929,503, dated Nov. 18, 2009.

Notice of Allowance/Allowability for U.S. Appl. No. 11/929,503, dated Dec. 1, 2009.

International Search Report for PCT/US07/083075, dated Sep. 9, 2008.

International Preliminary Report on Patentability and Written Opinion for PCT/US07/083075, dated May 5, 2009.

Meukam et al., "Experimental Optimization of a Solar Still: Application to Alcohol Distillation," Chemical Engineering and Processing 43:1569-1577 (2004).

Matthijs et al., "Application of Light-Emitting Diodes in Bioreactors: Flashing Light Effects and Energy Economy in Algal Culture," Biotechnology and Bioengineering 50:98-107 (1996).

* cited by examiner

Photobioreactor Apparatus Designs

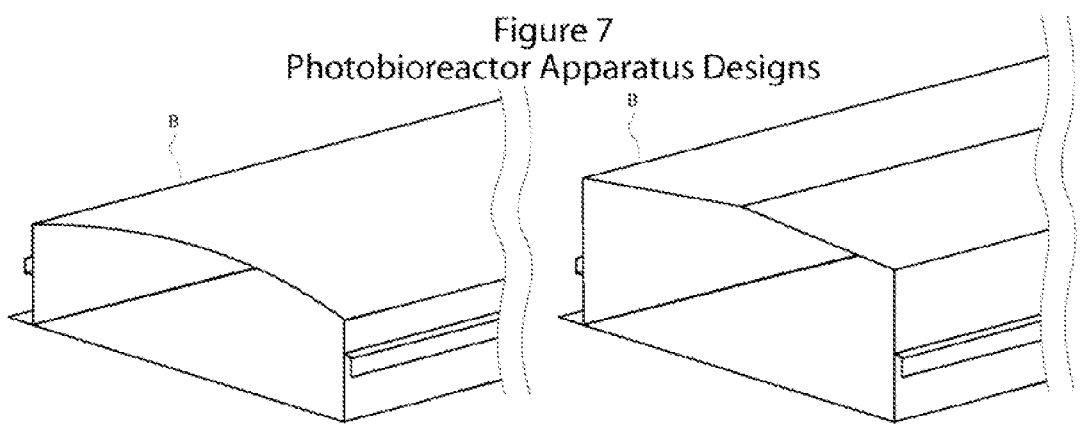
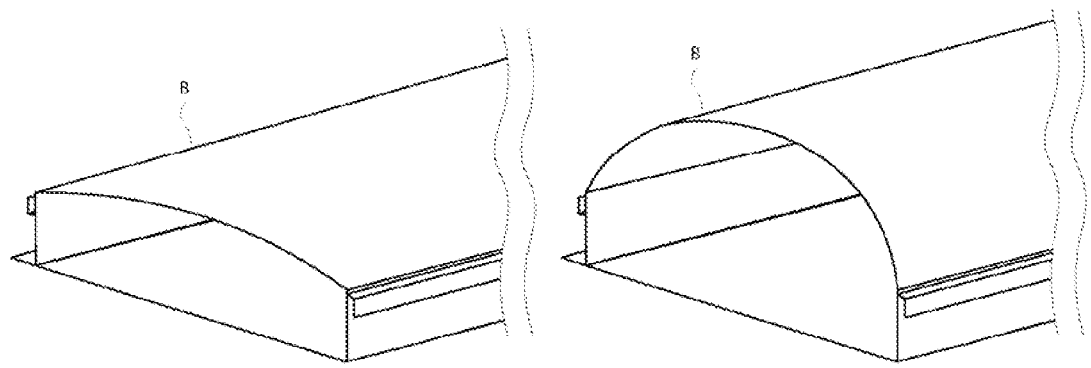
Figure 7
Photobioreactor Apparatus Designs

Installed Photobioreactor Apparatus

Installed Photobioreactor Apparatus

Sample Photobioreactor Apparatus End Plugs

Photobioreactor Apparatus End Plug Installed

Photobioreactor Apparatus Dual Flow Connector

Photobioreactor Apparatus Dual Flow Connector

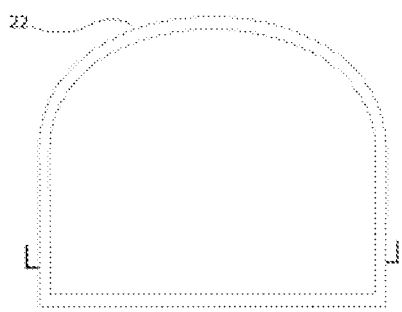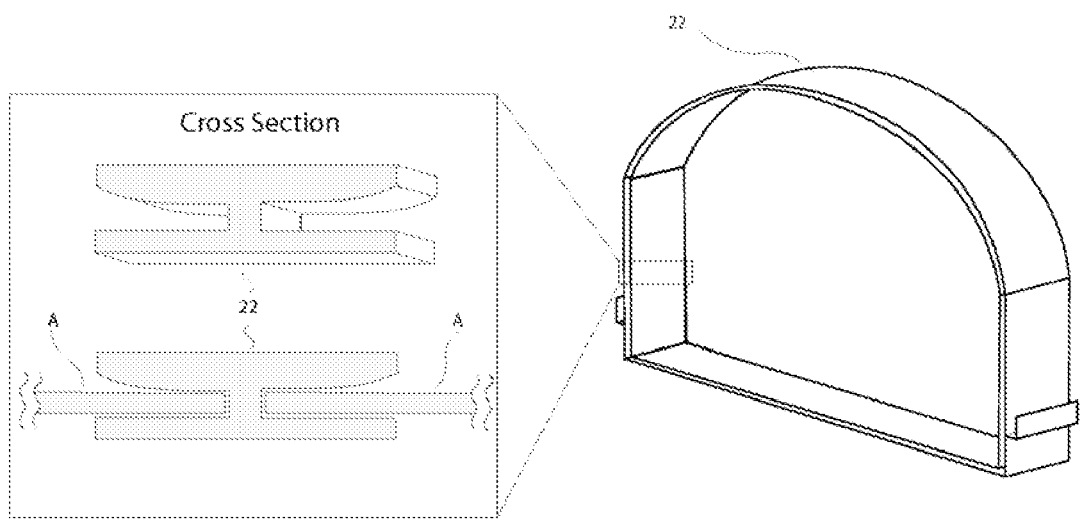
Figure 14
Photobioreactor Apparatus Coupling

Photobioreactor Apparatus Coupling Installed

Figure 16  Photobioreactor Apparatus Baffle Design Samples

Figure 17 Photobioreactor Apparatus Baffle Design Samples

Figure 18  Photobioreactor Apparatus Baffle Design Samples

Figure 19  Photobioreactor Apparatus Baffle Design Samples

Photobioreactor Apparatus Vent/Intake Samples

Photobioreactor Apparatus

Plastic Film Photobioreactor

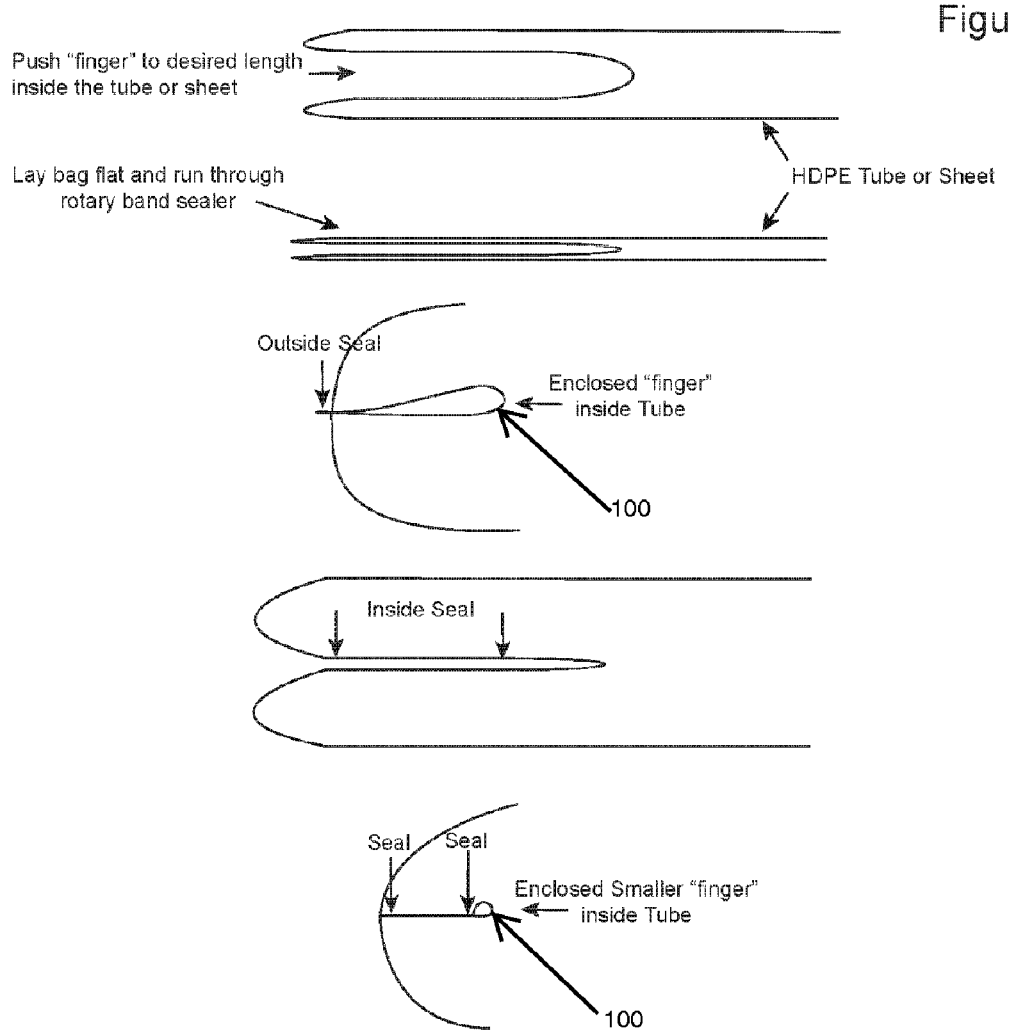

1

CLOSED PHOTOBIOREACTOR SYSTEM FOR CONTINUED DAILY IN SITU PRODUCTION OF ETHANOL FROM GENETICALLY ENHANCED PHOTOSYNTHETIC ORGANISMS WITH MEANS FOR SEPARATION AND REMOVAL OF ETHANOL

CROSS REFERENCE TO RELATED APPLICATIONS

This application is a continuation-in-part application of the prior application to Woods et al., titled "Closed Photobioreactor System for Continued Daily In Situ Production, Separation, Collection, and Removal of Ethanol from Genetically Enhanced Microorganisms," application Ser. No. 11/929,503, filed Oct. 30, 2007, now U.S. Pat. No. 7,682,821, which in turn claims the benefit of U.S. Provisional Application No. 60/864,091, filed Nov. 2, 2006. The text of both applications is incorporated by reference herein to the extent that there is no consistency with the present disclosure.

BACKGROUND

The invention relates to the fields of engineering, microbiology, marine biology, physical chemistry, and fluid dynamics.

The invention provides for an outdoor large volume closed photobioreactor for the continued daily production of ethanol, or other biofuels, from a culture media comprising genetically enhanced cyanobacteria or algae and in situ separation of the ethanol from the culture media through evaporation by sunlight and subsequent condensation and ethanol collection in the photobioreactor. The photobioreactor apparatus is designed to allow for the maintenance of a high density, stable culture comprising genetically enhanced cyanobacteria or algae and separation and collection of the ethanol produced in the same apparatus. An embodiment of the invention is the removal of ethanol from the culture comprising genetically enhanced cyanobacteria or algae, wherein the ethanol is removed from the culture without additional external manmade energy.

Given the high and escalating cost of fossil fuel based transportation fuels, the enormous world-wide demand for such fuels and the negative environmental impact of the widespread use of these fuels, there has been a significant market driven shift to the use of alternative fuels that are cleaner and renewable, namely biofuels. Currently, the production of biofuels, particularly ethanol, is dominated by the conversion of high cost feed substrates such as sugar cane, corn, rapeseed, palm oil and other terrestrial crops predominantly used as food for human/animal consumption. While the technology exists to convert these feedstocks to ethanol and biodiesel for use as transportation fuels, there is not sufficient arable land or fresh water resources to meet the enormous demand of the global transportation fuels market. The United States alone uses over 140 billion gallons of gasoline for transportation fuel per year. The current U.S. output of ethanol made from corn is over 5 billion gallons annually. The economic impact of the diversion of significant amounts of corn from the human/animal food market to the transportation fuels market has caused a greater than 50% increase in the market price of corn on global commodity markets. Such impacts on food commodity markets are not sustainable in the long-term, and large amounts of effort are being expended to find renewable alternatives that are cheaper and have the potential for larger scale production.

The most predominant alternate technology being developed is biomass conversion, namely the conversion of cellulose based waste products to biofuels using an industrial process. There remain significant technical challenges to bring this technology to a commercial reality. Given the high cost of the transportation of the cellulose feedstock to the processing facility and high capital costs, this technology could be limited in scale to facilities that can produce 5-100 million gallons of biofuel annually. Therefore, there is and will remain a need for an industrial biofuels production technology that does not use or displace a feedstock that is for human/animal consumption, does not use arable land, can be made in very large quantities at a low price, and does not use precious fresh water resources. One such technology is the use of genetically enhanced photoautotrophic cyanobacteria, algae, and other photoautotrophic organisms to convert internal sugars directly to ethanol, butanol, pentanol and other higher alcohols and other biofuels.

For example, genetically modified cyanobacteria having constructs comprising DNA fragments encoding pyruvate decarboxylase (pdc) and alcohol dehydrogenase (adh) enzymes are described in U.S. Pat. No. 6,699,696 (Woods, et al. for "Genetically modified cyanobacteria for the production of ethanol, the constructs and method thereof"). Cyanobacteria are photosynthetic bacteria which require light, inorganic elements, water, and a carbon source, generally carbon dioxide ($CO_2$), to metabolize and grow. The process using technology described in Woods, et al. has enabled the development of the industrial production of ethanol on a massive scale using readily available, cheap feed substrates, namely water and $CO_2$. The production of ethanol using genetically engineered cyanobacteria has also been described in PCT Published Patent Application WO 2007/084477 (Fu et al. for "Methods and Compositions for Ethanol Producing Cyanobacteria").

The production of biofuels using genetically enhanced photoautotrophic cyanobacteria, algae, and other photoautotrophic organisms opens a new realm in the industrial production of biofuels. The primary benefit of this technology is the combining of the process of the conversion of solar energy into cellular biochemical energy (the production of internal cellular "sugars") with the fermentation of these internal "sugars" directly into ethanol in one single cell. This "direct-to-ethanol" approach eliminates the need to separately grow and harvest the feed substrate then convert it to the biofuel. Other benefits of such a technology are the ability to use non-arable, non-productive marginal or desert land for production facilities, the ability to use saltwater, brackish water, fresh water or polluted water as a feed substrate, the ability to recycle enormous amounts of carbon dioxide into a transportation fuel and the ability to build massive scale production facilities with millions to billions of gallons of annual production capacity, all based on a genetically enhanced photoautotrophic organism.

Photoautotrophic organisms are those that can survive, grow and reproduce with energy derived entirely from the sun through the process of photosynthesis. Photosynthesis is essentially a carbon recycling process through which inorganic carbon dioxide ($CO_2$) is combined with solar energy, other nutrients and cellular biochemical processes to synthesize carbohydrates and other compounds critical to life. Photosynthesis absorbs light in a limited range of the total solar spectrum, only in the wavelength range of 400-700 nm. This range only represents about half of the total solar energy. While at this time little can be done to expand the wavelength absorption range of photosynthesis, efforts can be made to optimize what energy can be absorbed.

In the open environment, the overall photosynthetic efficiency rarely exceeds 6%. A combination of factors including respiration during dark periods, the length of the photoperiod, the intensity and incidence of the light, the chlorophyll content, available nutrients and stress all further reduce the efficiency of open plants in the natural outdoor environment. In laboratory photobioreactors, it is possible to achieve a photosynthetic efficiency of greater than 24%. The goal of all photobioreactor production systems is to optimize the environmental conditions and fine tune the overall production process to achieve high biomass production and photosynthesis yields well beyond those capable in the natural environment and in open pond growing systems.

Previous efforts for larger scale production have focused on growing photoautotrophic organisms in open ponds or raceways that provide similar growing conditions found in nature. A major drawback of this approach is that growing conditions cannot be well controlled, resulting in uncertain production outputs, batch contaminations and uncertain manufacturing costs. These open systems are also not suited for efficiently cultivating the genetically enhanced (GE) organisms available today.

The current bottleneck for industrial photoautotrophic organism production is a lack of cost effective large-scale cultivation systems utilizing photobioreactors. Very high volumetric production is necessary to reduce the overall size of the installed production system as well as reduce the production and downstream processing cost. Key factors of such systems are a high biomass concentration per volume, high photosynthetic efficiency and the ability to have such systems use very little manmade energy. Designing cost effective, ultra large (millions to billions of gallons of annual production output) manufacturing systems that are needed to produce very large quantities of biofuels has been a major unsolved technical challenge to date.

Various studies have resulted in designs of closed photobioreactors for culturing photoautotrophic organisms utilizing various technologies. In these controlled environments, much higher biomass productivity was achieved, but the biomass growth rates were not high enough to offset the capital costs of the expensive systems utilized for the production of low cost biofuels. Research in this field has focused on developing photobioreactor systems of multiple designs including plate reactors (also known as flat panels), vertical gas-sparged photobioreactors, bubble column reactors, airlift reactors, external loop airlift reactors and tubular photobioreactors. Each of these systems allow for varying degrees of process control and optimization, resulting in improved growing conditions to achieve a predictable volume and cost. All of these systems have demonstrated the ability of higher volumetric biomass production when compared to open pond systems; however, all of these systems require significant external energy to operate the bioreactor systems. For biofuels production, it will be necessary to limit the amount of energy required to operate the system to ensure the greatest positive energy balance for the biofuels produced.

Photobioreactors are generally cylindrical or tubular in shape (pipe) (Yogev et al. in U.S. Pat. No. 5,958,761), are usually oriented horizontal, and require additional energy to provide mixing (e.g., pumps), thus adding significant capital and operational expense, they have no purposed airhead except that created by trapped $O_2$. Oxygen, produced by photosynthesis can also become trapped in these types of systems and negatively inhibit growth and biofuel production. Photobioreactors, such as bubble columns or airlifts, may be oriented vertically and agitated pneumatically which can reduce the need for fluid pumping. These bioreactors are primarily or solely for biomass accumulation. Some photobioreactor designs rely on artificial lighting, e.g. fluorescent lamps, (such as described by Kodo et al. in U.S. Pat. No. 6,083,740). However, photobioreactors that do not utilize solar energy, but instead rely solely on artificial light sources, require so much energy input as to not be practical or cost effective for industrial scale production of biofuels. Fu and Dexter (WO 2007/084477) used GE 6×26 watt bulbs to provide light to the Bioflo R® 110 bioreactor system.

Several studies of algae cultured in photobioreactors have used narrow-bore tubes arranged in parallel and horizontal to the ground and on racks. These typically contain feed and harvest points to produce the biomass and require large surface areas. These systems rely on churning provided by pumping the biomass/growth medium through the piping at various high velocities. The cost of pumping in these systems will preclude them from being used in the production of biofuels on a large scale. Such systems are also not practical on a very large scale such as covering hundreds, if not thousands of hectares due to the high cost of the piping systems.

Bubble columns are typically translucent, large diameter vertically oriented containers filled with algae suspended in liquid medium, in which gases are bubbled in at the bottom of the container. Since precisely defined flow lines are not reproducibly formed in very large systems, it can be difficult to control the mixing properties of the system, which can lead to low mass transfer coefficients, poor photomodulation and low productivity.

Airlift reactors typically consist of vertically oriented concentric tubular containers, in which the gases are bubbled in at the bottom of the inner tube. The pressure gradient created at the bottom of the minor tube creates an annular liquid flow upward through the inner tube and then downward between the tubes. The external tube is made out of translucent material, while the inner tube is usually opaque. Therefore, the algae are exposed to light while passing between the tubes and to darkness while in the inner tube. The light-dark cycle is determined by the geometrical design of the reactor (height, tube diameters) and by operational parameters (e.g., gas flow rate).

Airlift bioreactors can have higher mass transfer coefficients and algal productivity when compared to conventional mechanically stirred systems. Analogous to mammalian cell production, large bubbles results in poor mass transfer of critical gases. Bubbles that are too small result in greater shear near the point of bubble creation and, therefore, more damaged or killed cells. Both damaged and killed cells can release components into the growth medium, that if too high, can greatly impact the health and thus the productivity of the system. However, control over the flow patterns within a very large airlift bioreactor to achieve a desired level of mixing and photomodulation is difficult or impractical. The energy requirement for an airlift photobioreactor is typically much lower than that for a stirred system and may be suitable for higher value products than commodity transportation fuel, but even the pumping costs required for an airlift photobioreactor are too great for low value commodity transportation fuels.

Moreover, because of geometric design constraints in most current systems, cylindrical-photobioreactors suffer from low productivity when used for large-scale outdoor algae production, due to factors related to light reflection and auto-shading effects (in which one column is shading the other). This technology is impractical for use in producing low value commodity transportation fuels such as ethanol.

It is important for optimum facility design and engineering to understand that when growing photosynthetic organisms at high density, shading of cells by other cells will reduce overall solar absorption.

Mixing mechanisms present a challenge in a bulk bioreactor and can be problematic once the cells pass from the mixing area of the bioreactor to the solar collection tubes where photosynthesis occurs. A major challenge to scale-up in a photobioreactor systems is increased shear stress from mixing or turbulence that results in cell damage (Gudin C., Dhaumont D. 1991. "Cell fragility is a key problem of microalgae mass production in closed photobioreactors," Bioresource Technology 38:145-151). Cells are often more resistant to static hydrodynamic shear and less resistant to shear created by a liquid/air surface. Cell damage and lysis can occur at several points, including bubble creation, bubble rising and, as for mammalian cells, bubbles bursting at the liquid/air interface. Plant cell walls often contain cellulosic material that give them high tensile strength, but may have extremely low shear resistance. The fixed blade impellers or excessive airflows in airlift bioreactors produce high shear rates that result in cell breakage. The optimum level of turbulence for mixing, which creates shear stress for cells, is a result of fluid flow and gas velocity. As the cell density increases, the viscosity of the fluid rises, which works against uniform mixing and subsequent optimum mass transfer of nutrients. High airflow rates at high cell densities in an airlift bioreactor can result in shear becoming too great and cell breakage occurring. Algae, similar to other species of plants in suspension culture, vary in the resistance to shear. This has been a major challenge in developing a standard photobioreactor in which all cells can be grown.

Rapid alteration between high light intensities and darkness have consistently been shown to significantly enhance the efficiency of photosynthesis, with shorter cycles having greater effects (Matthijs, et. al. Application of light emitting diodes in bioreactors: flashing light effects and energy economy in algal culture. Biotechnol. Bioeng. 50:98-107). It has been speculated that the reduction of electron acceptors in photosystem II (PSII), with the corresponding oxidation of those acceptors in the dark, results in high solar energy capture during the light. A solar absorption tube system containing clear and dark areas with in-line mixers and an optimized residence time through fluid flow control should be capable of light to dark cycles from fractions of a minute to several minutes as dictated by the species of algae. A better way to get light dark transitions is to mix algae so they are alternately shaded by other algae or exposed to light. The overall efficiency of the system depends on its area and its output. A dark area is not contributing to output. The algae may be more efficient, but the system as a whole is not. But if shading by algae is used, light is always being absorbed by an active element. Janssen, M, et. al. (Scale-up aspects of photobioreactor s: effects of mixing induced light/dark cycles. J. Appl. Phycol. 12:225-237.) demonstrated that a light gradient, which occurs in natural sunlight over a typical day, has a significant impact on biomass yield from a given energy of light. It is expected that as one moves away from the equator, either north or south, that the light gradient will be more pronounced over the year, resulting in lower efficiencies when moving away from the equator. The design of many air-lift photobioreactors results in lower than expected biomass, even when carbon dioxide and other nutrients are increased. This is due to the physical design of most systems that facilitates medium length light/dark cycles, which have been shown to reduce biomass yield. Churning is too rapid in fast-moving airlift systems and bubble column systems.

Airlift systems can be designed to provide optimal mass transfer of oxygen and carbon dioxide, although at dry weight densities over 70 g/L maintaining adequate dissolved carbon dioxide becomes difficult. At high cell densities and during high rates of photosynthesis, the production of oxygen and the rapid utilization of carbon dioxide often required venting of the system. This becomes an issue in long sealed phototubes and is a primary reason that external loop phototubes have limited lengths when not vented. But these pipe or small diameter tube systems are predominantly for biomass production and ethanol as a directly produced product is not being made.

As early as 1959, Tulecke and Nickell, and in 1963 by Wang and Staba, produced 20 liter bioreactors for the culture of plant cells. In the early 1970's, Kato and his colleagues at the Japan Tobacco and Salt Public Corporation investigated the use of air in mixing up to 1500 liters. Later, a 20,000 liter system was used by Noguchi at the same corporation. In the mid-1980's, Wagner and Vogelmann demonstrated that the airlift system was superior to all others in providing good productivity and a well defined and controlled system of parameters, resulting in reproducible flow characteristics. They further suggested that fluid movement can be better controlled through the use of an internal draft tube through which the air mixture is bubbled. Although such systems can be scaled up significantly, their operation requires much external energy and they are therefore not cost effective for use as production systems for biofuels. In addition, mutual shading in vertical airlift systems has an impact on the total installed system capacity in a given footprint.

Javanmardian and Palsson (1991, High-density photoautotrophic algal cultures: design, construction, and operation of a novel photobioreactor system. Biotechnology & Bioengineering: 38, p 1182-1189,) developed an equation for the depth of light penetration. Applying this equation to a high density pond system suggests that at cell densities of 50 g/L, light penetration would be less than 2 mm. This demonstrates that light penetration clearly limits algal biomass production in typical open pond situations. Ogbanna and Tanaka (1997, Industrial-size photobioreactor s. Chemtech: 27(7), p 43-49.) demonstrated that photosynthesis is maintained with a light intensity of 7.3 μmol/m2/s. In addition, Lee and Palsson (1994, High-density algal photobioreactors using light-emitting Diodes. Biotechnology and Bioengineering: 44, p 1161-1167,) found that both light path and light intensity increased algal biomass production with light path possibly having a greater impact.

People have worked on ways to supplement natural light with artificial lighting in order to increase the efficiency of photosynthesis. Lee and Palsson (High density algal photobioreactors using light emitting diodes. Biotech. BioEng. Vol 44, 1161-1167:1994) used highly efficient light-emitting diodes (LED comprising gallium aluminum arsenide chips) to demonstrate that artificial light at specific wavelengths (680 nm monochromatic red light) could significantly increase the density of the cell culture. They found that supplementation with light at a wavelength of 680 nm would produce a cell concentration of more than 2×109 cells/ml (or more than 6.6% v/v) and an oxygen production rate as high as 10 mmol oxygen/L culture/h, using on-line ultrafiltration to periodically provide fresh medium. While this process is expensive and may be impractical for ultra large scales required in the production of biofuels, it did demonstrate the possibility of enhancing overall productivity through supplemental lighting.

Hu, et. al. (1998, Ultra-cell-density culture of marine green alga chlorococcum littorale in flat-plate photobioreactor.

Applied Microbiology Biotechnology: 49, p 655-662) reported producing 84 g/L algae in a flat plate photobioreactor with a light intensity of 2,000 microeinsteins per second per meter squared. In a review of the literature up to that time 3-12 g/L were the more typical cell densities obtained in photobioreactors.

Fernandez, et. al. (2001, Airlift-driven external-loop tubular photobioreactors for outdoor production of microalgae: assessment of design and performance Chemical Engineering Science 56 (2001) 2721-2732) reported the results of the design of an airlift system which incorporated 80 m of clear tubing (pipe) as a solar receiver. The system was able to maintain high density algal cultures and used little external power to drive the system. This system's overall design and operation makes it an attractive candidate for large scale production, but the solar receiver system has limitations for massive scale production.

All current photobioreactor systems have various limitations for use in the massive scale industrial production of low cost biofuels. Most systems are not feasible because of their need for significant amounts of external energy for optimal operation. Another problem with existing systems is the high cost of the materials to build the systems. Many are mounted on expensive metal racking systems and are not placed on the ground. The most significant problem of all existing photobioreactors is that they are designed to maximize the production of biomass. The existing photobioreactors concentrate on the cells reproducing by division and increasing in number and mass with the goal of harvesting the algae or biomass and extracting products form the biomass in separate steps, or using the biomass itself, or drying the biomass. Current photobioreactor systems have various limitations for use in large scale industrial production of low cost biofuels using genetically enhanced photosynthetic microorganisms that make biofuels. Most systems are not feasible because of their need for significant amounts of external energy for optimal operation. Another problem with existing systems is the complexity and high cost of the materials to build the systems. Tube or pipe systems are traditionally made from acrylic or polycarbonate, and that is very expensive and not suited to large scale production. In additional the pipe or tube systems are placed on heavy metal racking to support the liquid culture off the ground, and that is also very expensive. Existing photobioreactors are designed to maximize the production of biomass. Existing photobioreactors concentrate on the optimization of biomass production through reproducing the cells by division and increasing in number and mass, or a particular lipid or protein with the goal of harvesting the microorganisms or biomass from the photobioreactor and then extracting the desired products from the biomass. Harvesting the product from the biomass requires significant energy and effort and typically requires that the microorganisms or biomass be replaced for the next cycle of biofuel production. Preferably, a photobioreactor system using genetically enhanced photoautotrophic organisms for the production of ethanol would collect the produced biofuel without having to remove the microorganisms or biomass from the photobioreactor. Traditional photobioreactors are unable to do this as they are designed to produce biomass and this would require the biomass to be harvested or separated from the water, saccrified and processed in many steps to get and end product of ethanol or lipid. In addition, cell division requires a significant amount of the cell's available biochemical energy. It is therefore desirable to maintain the culture in a steady state and convert as much cellular biochemical energy to ethanol as possible. Current bioreactor systems are not typically designed to maintain steady state cultures. Current industrial photobioreactor systems do not have a means for trapping ethanol produced by genetically enhanced photosynthetic microorganisms which is released directly into the culture medium. Therefore, in current bioreactor systems, the ethanol in the culture medium would be vented to the atmosphere while removing the saturated or supersaturated levels of $O_2$ produced during photosynthesis volatilizing out of the culture medium.

To solve the problem of the inefficiencies involved in recovery of biofuels such as ethanol from harvested biomass in photobioreactors, the present invention overcomes the external energy usage and materials constraints of existing photobioreactor systems while maintaining the need for culture control and gas exchange necessary for maintaining high-density cultures for low cost biofuels production. Current systems have large requirements for energy to grow and maintain biomass. The present invention uses solar energy and only small amounts of manmade energy. The present invention provides for recovery of the biofuel from condensate in an upper portion of the photobioreactor and/or from a gas exhaust stream from an upper part of the chamber. The present invention uses a large airhead space above the culture medium as a means of allowing the ethanol to evaporate from the culture medium and enter the gas phase of the apparatus. The ethanol can then condense on the walls of the upper part of the apparatus and run into collection troughs, or the gas phase can be collected as it leaves apparatus and the ethanol enriched gases can go through external means of collecting the ethanol from the gas phase. As $O_2$ is produced by the organisms in the culture, and any small trace amounts of excess $CO_2$ introduced into the culture escape, and as water is changed from a liquid phase to a gas phase, $O_2$ and ethanol gas, in addition to the ethanol in the condensate, will be pushed from the photobioreactor and the ethanol must be recovered in order to maximize the efficiency of the system. In the present invention this can be accomplished predominately with solar energy.

Furthermore, the present disclosure provides for recovery of the biofuel from condensate in an upper portion of the photobioreactor and/or from a gas exhaust stream from an upper part of the chamber. The apparatus and methods disclosed herein allow for at least approximately 80% to about 100% of the total biofuel product to be recovered by condensation from the upper portion of the photobioreactor and/or an exhaust gas stream with no recovery or at most only about 1% to about 20% of total biofuel production to be recovered from the biomass in a lower portion of the photobioreactor.

The production of biofuels using genetically enhanced photoautotrophic organisms on an industrial scale requires photobioreactor systems which cover hundreds, if not thousands, of hectares of land and contain millions, if not billions of gallons of water for organism growth. Such systems have never before been developed and pose significant engineering challenges. Because the product being produced is a low cost commodity, not a high value product, low manufacturing costs are critical for overall commercial success. This one constraint alone effectively eliminates all current designs of industrial sized photobioreactor systems for the manufacture of biofuels on a large scale. The current invention allows for photobioreactor systems which can efficiently produce biofuels from genetically enhanced photosynthetic microorganisms on a massive scale at low cost.

When exposed to sufficient light, such as sunlight, the genetically enhanced organisms release the biofuel into the aqueous growth medium where it evaporates as a gas into the upper part of the chamber. The water and biofuel condense on the inner surface of the upper part of the chamber and the droplets run down the internal surface into a collection trough, which in one embodiment uses gravity to drain to a lower area for distillation. Although this evaporation and condensation will happen continuously during the day, the greatest production of evaporation and condensation will most likely be at night during the time when there is a greater temperature differential between the inside of the bioreactor and the outside ambient air temperature.

Because the genetically enhanced organisms release the biofuel into the surrounding growth medium where it evaporates, none or very little of the culture has to be harvested or removed to recover the biofuel. This results in significantly increased efficiency and net energy gain from the system compared to photobioreactor systems that have to expend resources to remove most or all of the culture from the photobioreactor, separate the biomass from the culture, process the biomass by centrifugation or saccrification to extract a product, then new organisms have to be cultured and inoculated, and then the organism is replaced in the culture in the photobioreactor. None of these steps are trivial or inexpensive.

The photobioreactors and methods disclosed herein are especially applicable for use as large-scale outdoor photobioreactors, where sunlight is utilized as the light source. The term "large-scale" in reference to photobioreactors means photobioreactors having a volume greater than about 1,000 liters, or in some embodiments, greater than about 10,000 liters. The photobioreactors comprise closed shapes that can be any shape including but not limited to those with rectangular, triangular, cylindrical, circular, oval, irregular or polygonal cross-sections. The photobioreactors can be tube shaped, hexagonal or multisided domes, or circular domes. The photobioreactor is closed to the surrounding environment in the sense that loss by evaporation of biofuel is kept low and order to prevent: and to prevent contamination from heterotrophic bacteria and other organisms and their waste; evaporation of water; reduction in salinity changes; containment of the organisms; theft; and vandalism is minimized.

Biofuels able to be produced and released in the present invention include, but are not limited to, ethanol, butanol, pentanol and other higher alcohols. In a preferred embodiment, the biofuel is ethanol.

Constructs and methods for producing ethanol from genetically modified cyanobacteria have been disclosed (Ref: Woods et al., Fu/Dexter, Coleman et al.). These methods provide for the production and release of liquid ethanol into a culture medium from cyanobacteria exposed to sunlight and provided water, $CO_2$ and nutrients. Methods and devices exist for the growth, maintenance, and harvest of algal or cyanobacterial biomass from aqueous cultures on a small scale. Most are designed for use in a laboratory and use artificial light to stimulate photosynthesis. Methods for separating ethanol from aqueous solutions are also disclosed. These separation devices all require energy in the form of manmade externally generated power to drive the separation process, whether it results from heating (distillation) or cooling (pervaporation). There are no devices currently available or described that provide for the large scale, outdoor growth and maintenance of cyanobacterial cultures producing ethanol that also enable the separation of ethanol from the aqueous culture in the same apparatus where the cyanobacteria are being cultured, wherein certain embodiments are made cheaply, are driven by solar power, use diurnal variation in light and temperature, and are designed for controlling the amount of nutrients, light, water, and $CO_2$ to which the cyanobacteria are exposed.

The present invention solves these problems. It provides for an outdoor large volume closed photobioreactor for the continued daily production of ethanol from a culture media comprising genetically enhanced cyanobacteria or algae and separation of the ethanol from the culture media through evaporation by sunlight and subsequent condensation and ethanol collection in the same photobioreactor chamber in which the cyanobacteria grow. An embodiment of the invention includes the use of a single chamber composed of translucent plastic which contains a space for growing and maintaining the cyanobacteria in an aqueous culture medium, an airhead for evaporating the ethanol from the aqueous solution using sunlight, and a surface for condensing the ethanol from the evaporated gas. This embodiment has troughs for the collection of the condensed liquid ethanol that can then be moved through attached pipes to a separate apparatus for processing the ethanol to the desired purity. In another embodiment the upper part of the chamber of the photobioreactor has additional coolant compartments in thermal contact with the gas in the upper part of the chamber. A fluid coolant is passed through the coolant compartment that further cools the gas in the upper part of the chamber and enhances condensation of the biofuel into the collection troughs. The photobioreactor may be constructed as a single piece or as multiple pieces, such as a separate upper part of the chamber and lower part of the chamber, joined together, and in an embodiment is made from lightweight and inexpensive materials, including rigid materials such as extruded plastic, molded plastic domes, glass, fiber glass, plastic sheets or panels, and flexible materials, such as plastic film, or a combination of flexible and rigid materials. The upper part of the chamber is optionally coated with a material or constructed from materials that selectively filter out wavelengths of light. For example, the upper part of the chamber can be coated or constructed from a material that filters out potentially harmful UV light and/or only transmits a specified wavelength range optimal for photosynthesis by the organisms in the bioreactor.

The photobioreactor can contain ports for the injection of carbon dioxide or other gases. The injection of gas is designed to produce churning of the aqueous culture. Churning and mixing in the growth medium allows higher density cultures and higher biofuel production by minimizing the effects of mutual shading. Churning and mixing also provides for increased gas exchange from the growth medium to the gas phase in the upper part of the chamber and from the gas phase to the growth medium. Since oxygen is known to inhibit photosynthesis, removal of the oxygen produced during photosynthesis from the growth medium helps to optimize biofuel production. Churning also helps the carbon dioxide in the gas phase pass to the growth medium to support carbon fixation and increase biofuel production. Churning can be controlled through the use of baffles and dams, mixing devices, injection of gases such as carbon dioxide through the growth medium, as well as by the liquid flow through the photobioreactor. Excess oxygen in the growth medium or in the gas immediately above the culture can inhibit the cellular production of ethanol or other biofuels. Accordingly, ports or outlets can remove excess oxygen.

Thus, the current invention is a device that provides for the large scale, outdoor growth and maintenance of cyanobacterial cultures producing ethanol that also enable the separation of ethanol from the aqueous culture in the same apparatus where the cyanobacteria are being cultured, wherein certain embodiments are made cheaply, are driven by solar power, use diurnal variation in light and temperature, and are designed for controlling the amount of nutrients, light, water, and $CO_2$ to which the cyanobacteria are exposed. One notes that the approach disclosed herein is not mentioned in the review article by C. U. Ugwu, et al., Photobioreactors for Mass Cultivation of Algae, 99 Bioresource Technology 4021 (2008).

The above discussion includes both information known to the art prior to the filing date and information forming part of the present inventive disclosure. Inclusion of any statement in this section, whether as a characterization of a published reference or in a discussion of technical problems and their solutions, is not to be taken as an admission that such statement is prior art.

SUMMARY OF THE INVENTION

This invention is directed to a photobioreactor closed from the outside environment comprising a chamber which comprises: a headspace; an upper part of the chamber which comprises a translucent or clear region to allow in sunlight: a lower part of the chamber which comprises an aqueous growth medium comprising a culture of genetically enhanced organisms disposed in the growth medium, wherein said organisms are selected from the group consisting of algae and cyanobacteria, and wherein said organisms produce ethanol on a continued daily basis which enters the growth medium; wherein the ethanol in the growth medium evaporates into the headspace, condenses on the inner surface of the upper part of the chamber, and collects in a collection trough and the chamber possesses a plurality of openings for inlet and outlet tubes.

An embodiment of the invention is based on the discovery that the ethanol concentration in the collection trough can be greater than the ethanol concentration within the aqueous growth medium. The present invention is distinct from the prior art in that the inside surface of the upper part of the chamber is functioning to condense ethanol from the gas phase to the liquid phase. Previous approaches, such as that embodied in Fu and Dexter WO 2007/084477, condense gas phase material to liquid phase material, using only a condenser located outside the chamber. The present invention thus gives a new function to the upper part of the chamber, a surface upon which gas phase material can condense to the liquid phase, in addition to the function of allowing light to enter the chamber. Separately, the result that the condensed ethanol in the upper chamber is enriched in ethanol relative to the content of ethanol in the liquid phase of the aqueous growth medium of the lower chamber is unpredictable and unexpected. Within the chamber, in the limit of obtaining thermodynamic equilibrium, the concentrations of ethanol would be the same in both liquid phases (that of the collection trough and that of aqueous growth medium). The collection trough of the present invention allows one to capture the unexpected benefit.

A further embodiment is an apparatus for the continued daily production of ethanol and oxygen from carbon dioxide and water in a closed reaction volume, wherein: the reaction volume comprises a liquid-phase volume and a gas-phase volume; the carbon dioxide and water is converted to ethanol and oxygen in the liquid-phase volume by genetically-modified microorganisms selected from the group consisting of algae, cyanobacteria; the ethanol, water and oxygen enter the gas phase and occupy the gas-phase volume; the ethanol and water in the gas-phase volume are condensed to a condensate volume wherein the concentration of the ethanol in the condensate volume is higher than the concentration of ethanol in the liquid-phase containing the microorganisms A further embodiment is an apparatus for the production of ethanol and oxygen from carbon dioxide and water comprising modular plastic extrusions, at least partially clear or translucent on top, mounted on soil; a liquid phase reaction volume; a head space volume; a means of introducing carbon dioxide to the liquid phase reaction volume; a means of converting the carbon dioxide into ethanol and oxygen within the liquid phase reaction volume, wherein oxygen goes from the liquid phase reaction volume into the head space volume; a means of separating ethanol from the liquid phase reaction volume by forming gas-phase ethanol followed by condensation of the gas-phase ethanol to liquid-phase ethanol which the condensed liquid-phase ethanol flows to a collection volume.

A further embodiment of the invention is an apparatus with a chamber comprising a container comprising a mixture comprising liquid phase ethanol and liquid phase water, comprising a head space comprising gas phase ethanol and gas phase water, comprising an inner surface on which gas phase ethanol and gas phase water can condense, and a collection trough for collecting said condensed ethanol and water, wherein the concentration of ethanol in the collection trough is higher than in the container which comprises the liquid phase culture medium.

A further embodiment is a method of producing ethanol comprising: placing a culture of genetically enhanced organisms capable of producing ethanol selected from the group consisting of algae, cyanobacteria in a photobioreactor, wherein said photobioreactor comprises: a) a lower part of the chamber containing an aqueous growth medium, and b) a gas-filled upper part of the chamber, wherein the upper part of the chamber is at least partially translucent; allowing ethanol to evaporate from growth medium into the upper part of the chamber; condensing the evaporated ethanol; and collecting the condensed ethanol in one or more collection troughs.

BRIEF DESCRIPTION OF THE DRAWINGS

The apparatuses and methods hereof will hereinafter be described in conjunction with the appended drawings, where like designations denote like elements.

FIGS. 6 and 7 also show three-dimensional views of different shapes and designs of photobioreactor tubes suitable with the present invention.

FIG. 14 shows three-dimensional, end and cross-sectional view of a photobioreactor coupling unit that is used to join two separate tube shaped photobioreactors with the flow continuing in one direction.

FIG. 24 illustrates various means to manufacturing condensate collection troughs into said photobioreactor.

DETAILED DESCRIPTION

Figure 1:
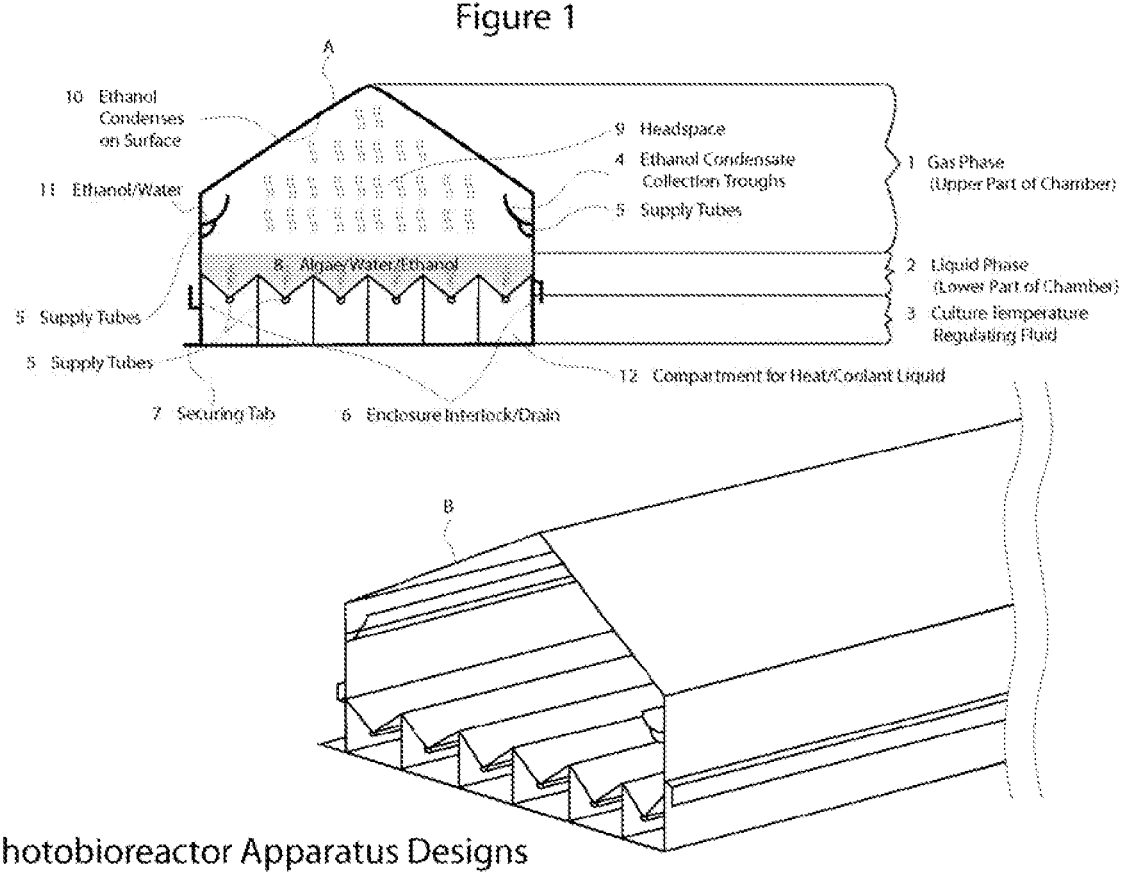
FIG. 1 shows a photobioreactor of the present invention having a rectangular tube shape, an upper and lower part of the chamber.

Disclosed herein are photobioreactor systems and methods that permit the culture of genetically-enhanced photoautotrophic organisms that can achieve high biomass densities and high photosynthetic conversion rates. In addition, combinations of known technologies that can control temperature, nutrients, gases and waste can be used herein. Such a closed, large-scale, large-volume, external solar receiver apparatus for outdoor photobioreactor systems for industrial scale production has not been shown heretofore, using natural sunlight to drive photosynthesis for biomass production and requiring minimal amounts of external energy to operate.

The design and operation of the total photobioreactor system is optimized for the removal of excess heat, to maintain correct pH, salinity, maximum ethanol evaporation, minimal water evaporation, to reduce or eliminate water loss to the environment, to limit the possibility of contamination and to permit the development of a substantial concentration of a biofuel such as ethanol in the growth medium, and to limit spontaneous mutations in the cultured organisms, and to regulate temperature, to maximize the total amount of organisms in the growth medium, to maximize the total amount of organisms in the growth medium that receive light by churning the organisms in the growth medium from the top to the middle and bottom and back to the top, to maximize the photosynthetic rate of the organisms by limiting light saturation and minimizing dark or shaded periods in the tube, and to balance the effect of saturation and shading, and to limit the effect of spontaneous mutations in the cultured organisms.

An embodiment of the photobioreactor provided herein has a shape and design that maximizes the incidence of solar energy absorption during photosynthesis. The photobioreactor design is engineered to reduce the daily variation of the temperature when placed on location at the production facility.

Designs for photobioreactors in the prior art are intended for the production primarily of biomass, and secondarily of products derived from the biomass. They require inputs of carbon dioxide, water, mineral nutrients and light. They have outputs of oxygen and biomass. As a practical matter they may also have outputs into the growth medium, which must be separated from the biomass, water vapor, and incidental components of the gas phase such as nitrogen. Methods have been disclosed for the production of hydrogen using cultures of organisms in a photobioreactor designed and operated for that purpose. Hydrogen producing photobioreactors provide an anaerobic environment in which hydrogen production occurs. There may be internal production of biomass that is consumed as part of the hydrogen production process. The only essential output is hydrogen, and the only essential inputs are water and light. The ethanol producing photobioreactor system of the present invention has inputs of carbon dioxide and water and light. As a practical matter, it may be necessary to introduce some mineral nutrients into the reactor to allow enough growth for cell replacement, but addition of mineral nutrients is not inherent in the design of the process as it is in a biomass producing photobioreactor. A method of reducing heterotrophs can be accomplished with a nutrient deficient growth medium.

The present invention provides for an outdoor, large volume, closed photobioreactor for the continued daily in situ production of ethanol from genetically enhanced cyanobacteria, or algae in culture, release of ethanol by evaporation from the culture into the headspace of the device, collection of ethanol by condensation, and removal of the ethanol through collection troughs in the device. Specifically, the photobioreactor comprises a chamber which comprises an upper part of the chamber which comprises a translucent or clear region to allow in sunlight and an inner surface of the upper part of the chamber on which inner surface ethanol and water may condense. The photobioreactor comprises a lower part of the chamber which comprises an aqueous growth medium comprising a culture of genetically enhanced organisms disposed in the growth medium. The chamber comprises a plurality of collection troughs for the collection of liquid phase materials. The ethanol collected in the collection trough can be of higher concentration than the concentration of ethanol in the growth medium.

The photobioreactor may be made of clear plastic or other translucent material molded into desired shapes such as extruded tubes or molded domes. The top of the photobioreactor is clear to allow sunlight through and photosynthesis to occur in the cyanobacteria or algae in culture. The enhanced cyanobacteria or algae in culture produce the ethanol intracellularly from sunlight, $CO_2$, water, and then release it to the culture medium. The photobioreactor is designed to promote evaporation of ethanol from the culture medium and then condense the ethanol into a liquid that can be captured in troughs and removed for further distillation. The upper inside part of the photobioreactor is where the ethanol condenses and collects to run to the troughs. The upper part of the chamber of the photobioreactor may have additional internal coolant chambers with fluid coolant passing through them to maximize the condensation of ethanol for collection in the troughs. The photobioreactor has inlets that allow for the introduction of water, $CO_2$, and nutrients, and outlets for the removal of ethanol, water, by-products, and $O_2$. The photobioreactor could be made without the internal coolant chambers including when conditions do not require the lower temperature to condense the ethanol. The upper part of the chamber may be divided into sections to allow heat to rise above and away from the culture. The upper part of the chamber may have materials applied to the surface that maximize the condensation of ethanol. The photobioreactor may be made in one piece or in multiple parts and assembled.

The lower part of the chamber contains the genetically modified cyanobacteria, algae or other photoautotroph culture that produces the ethanol. The lower part of the chamber containing the culture is shaped to allow for the easy mixing of the culture and nutrients by the bubbling of $CO_2$ and the increased dissolving of the $CO_2$ gas into the culture. The lower part of the chamber is also shaped to allow for the maximizing of the surface area and therefore contact with the bottom compartment filled with temperature regulating fluid and would serve to cool the culture in the heat of the day, and keep the culture warm at night. The lower part of the chamber also has rails to allow for the use of a mixing device if necessary. The lower part of the chamber has inlets incorporated in the sides and ends to allow for the introduction of nutrients and the return of water. The lower part of the chamber has multiple inlets incorporated in the bottom to allow for the bubbling of $CO_2$ gas. The bottom chamber, when needed, is filled with temperature regulating fluid. The photobioreactor could be made without the temperature maintenance compartment under the lower part of the chamber for use in moderate climates, but with the temperature maintenance compartments and the temperature regulating fluid, the photobioreactor can be adapted to higher temperatures in many marginal land and desert areas. The regulating properties of the photobioreactor allow for the proper conditions to be regulated and maintained for maximizing ethanol production during different times of the day and during changing seasons. In addition, the photobioreactor design permits the regulation of internal nutrients, by-products, gases, and optimizing ethanol production conditions in the culture. The photobioreactor can have culture monitoring and regulating devices attached to it.

The liquid growth medium can be any growth medium useful for the maintenance of a culture of cyanobacteria, and algae. For example, it can be an aqueous growth medium such as water only, water and carbon dioxide, or a solution comprising water, carbon dioxide and nutrients that are helpful or necessary for maintaining the culture. The photobioreactor has inlets that allow for the introduction of water and nutrients, and culture monitoring, measuring devices and regulating devices that can detect when the water and/or nutrient level in the lower part of the chamber fall outside a certain predetermined level. A controller takes corrective action and activates the pump or valve to regulate pumping or passing the water and/or nutrients through the inlet and into the lower part of the chamber to keep the levels within a certain predetermined range.

The current invention eliminates the need for such gas exchange systems by using a significant airhead (gas phase) space contacting the physical culture. When combined with a low energy mixing system and/or means for introduction of $CO_2$ by a bubbling system, $CO_2$ can be injected for use by the organisms and the $O_2$ released from the liquid phase to the gas phase space.

The design of the photobioreactor apparatus as part of a total bioreactor system is optimized for the removal of excess heat, to maintain correct pH and temperature, to limit evaporation to the external environment, to limit or control changes in salinity, to limit the possibility of contamination an and to permit the development of a substantial concentration of a biofuel such as ethanol in the growth medium, and to limit spontaneous mutations in the cultured organisms. The photobioreactor apparatus has a sufficient size to maximize solar energy absorption by the culture to facilitate maximum photosynthesis while covering the ground surface in an efficient manner to maximize photobioreactor apparatus surface area, maximize total facility ground coverage, minimize supply and service areas to lower overall installation cost.

The photobioreactor apparatus comprises an upper portion composed of a transparent or translucent material to allow for the passage of light to the inside of the apparatus. The inner face of the upper portion will be in contact with the gases supplied to the culture system, as well as the gases produced during photosynthesis. The lower portion of the photobioreactor apparatus may be made from the same material as the upper portion, but does not have to be composed of a transparent or translucent material.

During operation of the photobioreactor, cells can adhere to the walls of vessels and exhibit foaming. Foaming creates air pockets and cell adherence to the photobioreactor walls restricts solar light penetration and, thus, uniform absorption by the cells. Foaming may be mitigated through the use of antifoam agents, such as polypropylene glycol (PPG). Additionally, the inner surface of the photobioreactor is optionally treated with an anti-fouling material to prevent cell adherence.

Where ethanol production is best optimized by the mixing of the culture then several options exist in this photobioreactor, a mixing device may be added, or the culture may be pumped into one end where the apparatus can further comprise internal mixing means. For example, static mixers comprise of a series of internal flow baffles, which mimics the mixing and churning in a stream bed, while minimizing shear damage to the cultured organisms, to provide turbulent flow and appropriate mixing and churning of the culture to ensure uniform exposure of all of the cells to solar radiation. Moreover, the turbulent flow thus produced not only provides mixing for maximal photosynthesis, but also serves to remove dissolved oxygen and enhances absorption of carbon dioxide from the airhead above the culture. Internal static mixers or baffles can be used on systems which are installed on properly sloped surfaces that provide sufficient liquid flow to achieve the desired mixing and churning as well as sufficient residence time in the system to cost effectively produce ethanol. Static mixers are appropriate if a means of circulation is provided so that a flow of water exists. Static methods are only effective if there is a water flow. Optionally, the photobioreactor apparatus may be fitted with dams to control the flow of culture through the apparatus in areas where there is a slope to the surface where the photobioreactor is situated.

In physical locations where the land is flat or only slightly sloped, or if recirculation pumps are not used, it may be necessary with certain genetically enhanced photoautotrophic cyanobacteria or algae, to install an internal mixing systems. Such systems can have numerous designs, but they must be able to operate using minimal external energy while providing sufficient mixing for optimal ethanol production and gas removal. There are a wide variety of means for mixing fluids which could be adapted to mixing the culture within the reactor well known to those skilled in the art. For example those mixing means used in the design of non-photosynthetic bioreactors and operated at energy levels appropriate for fuel production could be used. Other mixing means not now used in bioreactors may also be applicable. The correct use of such mixers eliminates the high energy consumption associated with pumped circulation of growth medium common to many bioreactor designs.

But in most instances with genetically enhanced photoautotrophic cyanobacteria or algae, the photobioreactor is designed to maintain a static culture at high cell density, with minimum cell growth and division, with much of the energy flow from photosynthesis going to ethanol production and not mere biomass accumulation.

Excess oxygen must be allowed to escape. This can be accomplished by venting the gas phase. A small amount of ethanol will also be lost when oxygen is vented, unless oxygen venting uses one or more of the ethanol retention methods described below. In the event oxygen is particularly inhibitory to the organism in culture, it may be desirable to further reduce the oxygen level in the photosynthetic enclosure. This may be accomplished by several means. For example, a carrier gas such as normal air can be passed through the system so that the venting is more rapid than it would be by build up of oxygen pressure alone, so the steady state oxygen concentration is between normal atmospheric levels and 300% oxygen, with the actual level determined by the system design. Additionally the entire gas phase may be removed mechanically from above the culture and passed through a number of existing devices that extract ethanol from the gas phase, including a dephlegmator, cooling heat exchangers, or other forced extraction methods from the gas phase outside of the photobioreactor. Non-venting methods are also available, such as passing the gas phase past an oxygen permeable membrane. Reduced pressure, e.g. provided by a vacuum pump on the other side of the membrane provides a pressure gradient to drive oxygen, but not other gas phase components, through the membrane.

Since genetically enhanced photoautotrophic aquatic organisms release the ethanol they produce directly into the growth medium, there is a significant technical challenge to extract the ethanol using minimal external energy. One way to harvest the ethanol is to take some of the growth medium, and use well-established industrial ethanol purification methods, (distillation, for example) resulting in the production of ethanol, a waste water stream, and a dried residue that may have value in feed or other applications. If growth medium is removed, it must be replaced with fresh medium. Additional algae should be added to make up for that which was removed, unless internal growth is sufficient to make up for removed algae. Harvesting biomass from which to recover the biofuel requires external energy for moving the growth medium/biomass mixture, for physical organism separation, and separate biofuel extraction. The cost and energy required for this type of process makes it unfeasible for large-scale use. The present disclosure provides an alternate means to remove the biofuel from the photobioreactor without the need for moving the growth medium, pumping separating the organisms by filtration or centrifugation, producing the biofuel by saccrification and further processing. Although this is process can be done, it will require a lot of external energy for moving the growth medium/biomass mixture, for physical organism separation, and separate ethanol extraction.

The invention provides for an alternate means to remove the ethanol from the growth medium without the need for pumping and/or filtration using only the energy from the sun. This is accomplished by providing for a significant airhead (gas phase) space above the culture. This space allows the sun to cause evaporation of the ethanol and water into the airhead space. Since the space inside the bioreactor is hotter than the outside ambient air temperature, the water and ethanol vapor will condense on the inner surface of the top surface of the bioreactor. The water and ethanol vapor condensates on the inner surface of the photobioreactor apparatus and the droplets run down the internal surface and fall into a collection trough, which uses gravity to drain to a central collection area for distillation. Although this evaporation and condensation will happen all day, the greatest production will be at night during the time when there is a greater temperature differential between the inside of the bioreactor and the outside ambient air temperature. This method of removing the ethanol from the culture without moving or disturbing the overall culture is very important in reducing the overall energy needed for the production system.

If there is excess condensate, the excess can be returned to the bioreactors either as a fluid or evaporated in a gas stream. Another alternate method of ethanol harvest is to pump the gas phase to an external condensation unit that may serve one or many bioreactors, and provide a cooled surface on which condensation may occur, subsequently returning the cooled and ethanol depleted gas phase to the bioreactors. Cooling may be provided by any economical means, and energy costs may be minimized if desired by use of heat exchangers or the like. The temperature to which the gas stream is cooled must be less than the temperature of the bioreactors to get condensation, but it need not be so low that all or a large fraction of the ethanol is removed from the gas stream, since the gas stream in this case is not vented to the atmosphere, ethanol that is not condensed to liquid is not lost but returned to the system. The condensate collected in this manner would then be further purified by distillation or other means. A further modification of this method of ethanol collection and removal which may be valuable would be to pass the gas phase or a portion of the gas phase through a cold trap, which would result in the removal of essentially all of the ethanol from the gas phase. This portion of the gas phase could then be vented to the air to allow for removal of excess oxygen, or the oxygen could be collected and used. Heat exchangers and the like can be used to reduce energy costs associated with cooling. It may be worthwhile in the process of harvesting ethanol using the above methods to use a device such as a dephlegmator, which passes the gas phase through a temperature gradient with a condensation and evaporation process reminiscent of a still which results in the production of a liquid stream enriched in water and a gas stream enriched in ethanol, so that the condensed ethanol has greater purity and subsequent purification is simpler and less costly. It may prove most economical to use a combined approach, in which most ethanol is removed using the photobioreactor internal condensation, with a relatively high condensation temperature and very low operating costs for the bulk of ethanol removal, and to use the low temperature condenser with optional dephlegmator to process the smaller gas volume that must be removed to get rid of excess oxygen. It can be worthwhile in the process of harvesting ethanol using the above methods to use a device such as a dephlegmator. Such dephlegmator are known to the art, and pass the gas phase through a temperature gradient with a condensation and evaporation process reminiscent of a still, which results in the production of a liquid stream enriched in water and a gas stream enriched in ethanol, so that the condensed ethanol has greater purity and subsequent purification is simpler and less costly. Those skilled in the art will be able to design an optimal system using these components that provides for ethanol harvest and oxygen removal.

In geographic locations where internal heat in the photobioreactor apparatus has a negative affect on the culture growth, it may be necessary to have a separate compartment below the culture in the apparatus to have water that can be used to cool or heat the overall culture. This extra mass of water can also be used to regulate the natural day to night heat and cooling cycle in locations with wide daily temperature swings such as desert locations. Additional cooling may be necessary, especially during periods of hot weather or the midday high sun. Cooling can be provided by water evaporation, for example by placing or submerging the photobioreactor apparatus in a pond containing water, said pond having a surface exposed to the air so that evaporative cooling occurs. The photobioreactor apparatus is in turn cooled by contact with the cooling water. Many different arrangements are possible. Photosynthetic enclosures may be floated on the water surface, submerged or partially submerged, movable within the pond, or the water depth of the pond may be adjusted to get any desired degree of heat transfer and evaporative cooling. Rates of heat transfer, evaporation, pond temperature as a function of weather conditions and the like can be predicted by those skilled in the art and used to obtain the desired temperature in the photosynthetic enclosure. Alternatively, coolant, water or other convenient material, that can be passed through the bottom temperature maintenance compartment, may be pumped, flowed, or passed to a processing site and cooled by other means such as an evaporative cooling tower. Alternatively, water may be pumped from a cool location such as a deep ocean location, used for cooling, and then discarded.

Furthermore, it is not necessary to continue to increase the biomass of the culture in some embodiments. When the culture has reached a suitable size for the photobioreactor, the cellular activities should shift away from continued replication, which demands greater nutrient presence, and toward biofuel production.

Enclosures may be made of rigid materials such as extruded plastic, molded plastic domes, or plastic sheets or panels, or flexible materials, such as plastic film, or a combination of flexible and rigid materials. It may include framing members to impart strength or form to materials such as plastic extrusion, panels, or film that would otherwise have inadequate mechanical properties to create the desired structure.

The bioreactor must be provided with $CO_2$ and water to provide substrate for the photosynthetic conversion of $CO_2$ to sugar, which is then subsequently converted to biofuel within the cells and then dispersed into the medium. $CO_2$ can readily be introduced as a gas, either into the gas phase or bubbled into the medium, or by means of a liquid where the $CO_2$ is supersaturated dissolved in the liquid.

The photobioreactor may be constructed as a single piece or as multiple pieces, such as a separate upper part of the chamber and lower part of the chamber, joined together, and in addition, lower temperature maintenance compartments may be joined to comprise the apparatus, and in an embodiment nutrient requirements of a biofuel producing photosynthetic apparatus are preferably low, since the culture should be producing primarily biofuels devoid of mineral nutrient content. Nutrients may leak out of cells into the medium and be re-used. Unlike other nutrients, nitrogen is often present in low but significant levels in volatile form, so there may be a gradual loss of ammonia from the culture in the photosynthetic enclosure. If this is the case, it can be replaced, either in the gas or liquid phase.

The lower portion of the photobioreactor apparatus can be made from the same material as the upper portion, but does not have to be composed of a transparent or translucent material. Additionally, the apparatus can be made airtight and should be watertight, and all connections and fittings in the system should be kept to a minimum, and be designed to prevent contamination of the culture.

The upper part of the chamber or a significant portion of the upper part of the chamber is transparent or at least partially translucent. As used herein, "partially translucent" should be understood as permitting sufficient passage of light, particularly sunlight, into the photobioreactor to enable photosynthesis by photoautotrophic organisms within the photobioreactor. In embodiments hereof, the upper part of the chamber or a significant portion of the upper part of the chamber is clear, transparent, or partially transparent. The upper part of the chamber is optionally coated with a material or constructed from materials that selectively filter out wavelengths of light. For example, the upper part of the chamber can be coated or constructed from a material that filters out potentially harmful UV light and/or only transmits a specified wavelength range optimal for photosynthesis by the organisms in the bioreactor. Such materials used in construction and coatings of transparent and translucent devices are well known in the art.

The photobioreactor apparatus has a sufficient size to maximize solar energy absorption by the culture to facilitate maximum photosynthesis while covering the ground surface in an efficient manner to maximize photobioreactor apparatus surface area, maximize total facility ground coverage, and minimize supply and service areas to lower overall installation cost.

During operation of the photobioreactor, cells can adhere to the walls of vessels and exhibit foaming. Foaming creates air pockets and cell adherence to the photobioreactor walls that restricts solar light penetration and, thus, uniform absorption by the cells. Foaming can be mitigated through the use of antifoam agents, such as polypropylene glycol (PPG) and other antifoam agents known to the art. Additionally, the inner surface of the photobioreactor is optionally constructed or treated with an anti-fouling material as known in the art to prevent cell adherence.

Also during operation of the photobioreactor, cells can adhere to the walls of vessels and it is also known in the art that certain hydrophobic and hydrophilic substances promote beading or collection of condensing liquids on a surface. The inner surface of the upper part of the chamber is optionally constructed or treated with such a substance to promote condensation in the upper part of the chamber.

Churning and mixing in the growth medium allows higher density cultures and higher biofuel production by minimizing the effects of mutual shading. Churning and mixing also provides for increased gas exchange from the growth medium to the gas phase in the upper part of the chamber and from the gas phase to the growth medium. Since oxygen is known to inhibit photosynthesis, removal of the oxygen produced during photosynthesis from the growth medium helps to optimize biofuel production. Churning also helps the carbon dioxide in the gas phase pass to the growth medium to support carbon fixation and increase biofuel production. Churning can be controlled through the use of baffles and dams, mixing devices, injection of gases such as carbon dioxide through the growth medium, as well as by the liquid flow through the photobioreactor.

Figure 3:
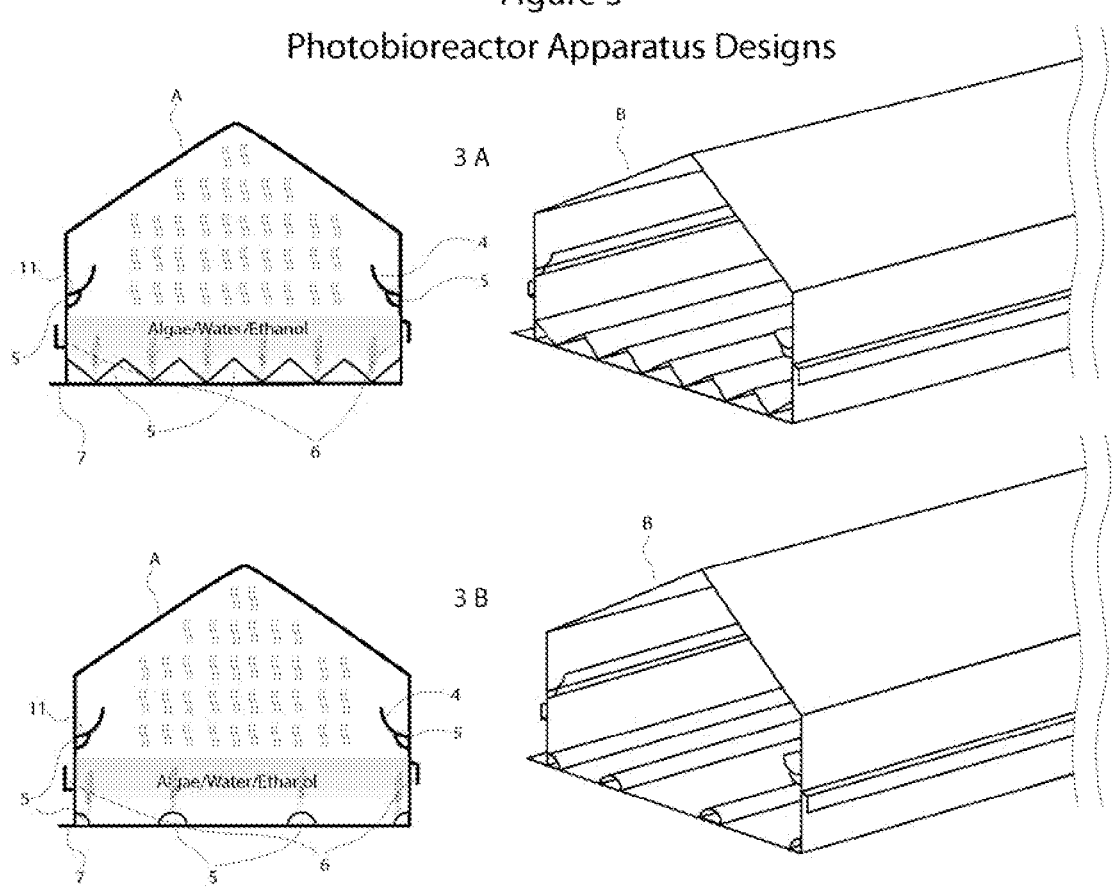
FIGS. 3A and 3B shows alternative photobioreactor designs for a tube shaped photobioreactor similar to the photobioreactor of FIG. 1. The alternative designs depicted in FIG. 3 do not contain means for heat exchange below the growth medium.
Figure 4:
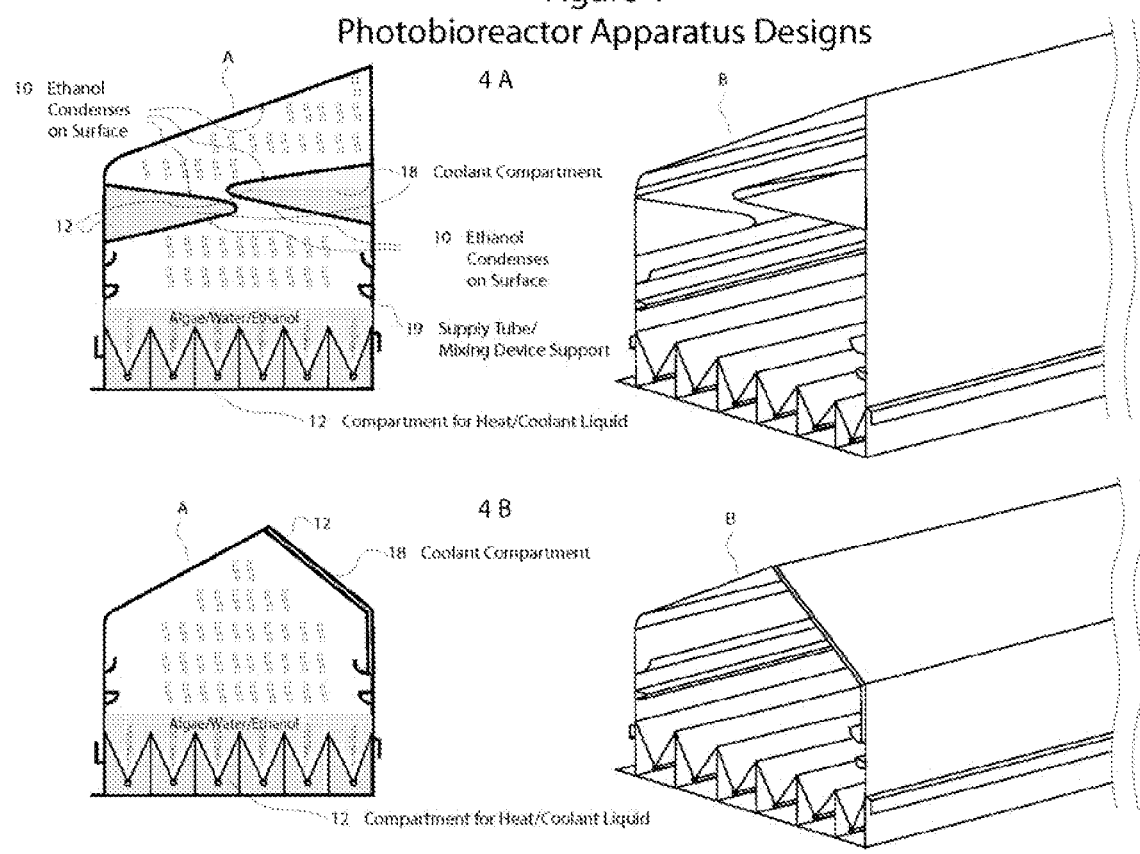
FIG. 4A shows a photobioreactor having two upper coolant compartments extending across the upper part of the chamber from the sides.
FIG. 4B shows a photobioreactor where the upper coolant compartment is a flat panel along the side of the chamber.

In one embodiment, a photobioreactor comprises an internal mixing means in addition to the carbon dioxide bubbling means. Providing mixing or churning in the growth medium ensures uniform exposure of all of the cells to solar radiation and evenly distributes nutrients and $CO_2$ in the growth medium. Moreover, the mixing and churning not only provides mixing for maximal photosynthesis, but also serves to remove dissolved oxygen from the growth medium and enhances absorption of carbon dioxide from the gas phase above the culture. Such churning and mixing systems can have numerous designs, but they should be able to operate using minimal external energy while providing sufficient mixing for optimal biofuel production and gas removal. There are a wide variety of means for mixing fluids, such as stirrers, which can be adapted to mixing the culture within the reactor by means well known to those skilled in the art. For example those churning and mixing means used in the design of non-photosynthetic bioreactors and operated at energy levels appropriate for fuel production could be used. Other mixing means used in fields other than bioreactors can also be applicable. The correct use of such mixers eliminates the high energy consumption associated with pumped circulation of growth medium common to many bioreactor designs. The lower part of the chamber can comprise rails or other support structures to allow for the use of a churning and mixing device. The lower part of the chamber is also optionally shaped to allow for the easy churning and mixing of the culture and nutrients by the bubbling of $CO_2$ and the increased dissolving of the $CO_2$ gas into the culture, such as by having a corrugated, sloped, or peaked bottom surface (as shown in FIGS. 1, 3a, and 4).

In a further embodiment, the photobioreactor can comprise static mixers, such as a series of internal flow baffles, which mimic the mixing and churning in a stream bed, while minimizing shear damage to the cultured organisms. Internal static mixers such as baffles can be used in systems that are installed on sloped surfaces to provide sufficient liquid flow to achieve the desired mixing and churning as well as sufficient residence time in the system to cost effectively produce ethanol. Static mixers are appropriate if a means of mechanical circulation is provided so that a flow of liquid exists on flat lands. Optionally, the photobioreactor apparatus can be fitted with dams to control the flow of culture through the apparatus in areas where there is a slope to the surface where the photobioreactor is situated.

Excess oxygen in the growth medium or in the gas immediately above the culture can inhibit the cellular production of ethanol or other biofuels. Accordingly, excess oxygen should be removed. This can be accomplished by venting or removing the gas from the upper part of the chamber. Enough oxygen should be removed to prevent inhibition of biofuel production below levels that are economically sustainable. For example, oxygen concentration within the lower part of the chamber should generally be kept below the level that would cause oxygen inhibition in that particular culture. Gas can be removed mechanically from above the upper part of the chamber culture through an oxygen exhaust outlet positioned in the upper part of the chamber. Additionally, gas, including excess oxygen and evaporated biofuel, can be removed from the upper part of the chamber and passed through a number of gas collecting devices known to the art that extract the biofuel from the gas phase, including a dephlegmator, cooling heat exchangers, or other forced extraction methods from the gas phase, which can be located outside of the photobioreactor. Non-venting methods are also available, such as passing the gas phase past an oxygen-permeable membrane. Reduced pressure, e.g., provided by a vacuum pump on the other side of the membrane, provides a pressure gradient to drive oxygen, but not other gas phase components, through a membrane separator. Excess pressure in the photobioreactor could have the same effect and push $O_2$ from inside the photobioreactor. Additionally, a preferred embodiment of the apparatus may be made airtight and must be watertight. In addition, all connections and fittings in the system should be kept to a minimum, and must be designed to prevent contamination of the culture. Additionally, a preferred embodiment of the apparatus is that one or more inlet or outlet, supplies, and drains tubes, may serve one or more functions.

In addition, to provide a large-scale photobioreactor while ensuring that the energy required to produce the biofuel product is less than the energy value of the produced biofuel, it is necessary to minimize manmade energy inputs for the creation of the biofuel, and recovery of the biofuel. No current photobioreactor uses solar energy to create, separate and recover the biofuel. The present invention can be accomplished predominately with solar energy.

In no existing photobioreactor does there exist the capability of producing a biofuel that is released and volatilized from the culture, removed and collected from the photobioreactor without harvesting the algae biomass. The key features that distinguish the invention from previous bioreactor designs are: (1) It is intended to produce biofuels directly, with the production of little or no biomass, nor harvest of the biomass (2) The biofuels produced, such as ethanol, may be volatile, so provision is made to prevent excess loss of biofuels in the gas streams associated with the removal of oxygen (3) Costs including energy inputs are reduced so that fuels can be offered at a price substantially less than those available from other bioreactor systems (4) Unlike corn and sugarcane derived ethanol that are separately grown, harvested, processed, and then their sugars are converted into ethanol in separate processes, the invention allows for a single container to grow the ethanol producing genetically enhanced photoautotroph, release the ethanol, collect, and remove the ethanol.

The chamber is the structure of the apparatus that contains both the liquid culture media and the headspace. The volume of the headspace is defined by the contours of the inside of the upper part of the chamber and the upper surface of the liquid culture media, as shown in FIG. 1. Ethanol and $H_2O$ gas contained within the headspace condense on the inner surface of the upper part of the chamber.

The headspace contains the gases above the culture and would include each of air, $CO_2$, $O_2$, $H_2O$ and ethanol.

The upper part of the chamber contains the headspace and the condensate. The upper part of the chamber can be divided into multiple smaller parts. The upper part of the chamber can contain coolant compartments that further facilitate condensation.

The coolant compartments of the upper part of the chamber are in thermal contact with the headspace in the upper part of the chamber, and comprising a coolant, wherein the coolant could be selected from the group including water, seawater or other coolant known to a person of ordinary skill in the art.

The lower part of the chamber contains the liquid culture media and this comprises the water, seawater, brackish water or polluted water, the genetically enhanced cyanobacteria or algae, the nutrients which could be selected from the group including nitrogen, nitrates, phosphates, ammonium, BG-11, $CO_2$, carbonates, trace elements, agents to promote the growth of the organisms, solutes selected from the group consisting of nutrients, fertilizers, antibiotics, and algaecides.

A list of measuring devices and sensors shall include pH, $CO_2$, $O_2$, temperature, salinity, and ethanol probes and sensors, and others know to a person skilled in the art.

The reason for using UV blocking and stabilizing agents, coatings or films, incorporated into the plastic or on the surface of the plastic is to include reducing heat in the culture, and breakdown of the plastic, and mutations of the organisms.

The design and operation of the total photobioreactor system is optimized for the removal of excess heat, to maintain correct pH, salinity, evaporation and temperature, to reduce the possibility of contamination, to maximize the total amount of organisms in the growth medium that receive light by rolling the organisms in the growth medium from the top to the middle and bottom and back to the top, to maximize the photosynthetic rate of the organisms by limiting light saturation and minimizing dark or shaded periods in the pipe, or to balance the effect of saturation and shading, and to limit the effect of spontaneous mutations in the cultured organisms.

The preferred embodiment of the present invention is a length and design that maximizes the incidence of solar energy absorption during photosynthesis. The photobioreactor geometry is engineered to reduce the daily variation of the solar irradiation when placed on location at the production facility. The headspace over the culture also serves to moderate the heat during periods of high solar radiation.

As part of the photobioreactor system, internal static mixers provide appropriate mixing, which is critical to ensuring uniform exposure of cells to solar radiation. Linear flow through solar tubes can reduce the overall photosynthesis since cells near the middle or bottom of the tubes receive less light than those towards the top. The present invention overcomes this limitation through the use of internal flow baffles designed to facilitate mixing. These flow baffles are static in nature, thus requiring no additional energy input beyond the flow rate determined by gravity. The careful balancing of mixing in the pipes with creating turbulent flow is important, since the algae cells are sensitive to sheer damage during heavy mixing. The design of the photobioreactor apparatus mimics the mixing and churning in a natural stream lined with rocks. The turbulent flow in the photobioreactor not only provides the necessary mixing for maximal photosynthesis in high density cultures, but also serves to remove dissolved oxygen and enhances absorption of $CO_2$. This also helps to stabilize the culture pH and increases the resident time of the biomass in the photobioreactor for photosynthesis.

The photobioreactor may also be fitted with dams of varying heights that can be used to control the flow of the culture in areas where there is a greater natural slope. This permits steeper surfaces to be used for production facilities and lower overall installation costs.

In addition, the dams can increase churning for cultures which grow in higher densities and need more mixing. The dams also serves as a control mechanism for growth medium and photoautotrophic organism output by maintaining an output at the end of the photobioreactor equal to input at the beginning of the photobioreactor while on a slope.

The dam serves as an inexpensive control mechanism for the time the organism spends in the photobioreactor tube. The dams also serve as a control of growth medium pressure that would occur at the bottom of a slope in a normal pipe. The dam allows for the photobioreactor to be placed on a slope and eliminates the need for mechanical mixers and stirrers that add to the cost the biofuels production. The growth medium and photoautotrophic organism can be pumped or poured by gravity into the top of the sloped apparatus without further need for mixing, or pumping while in the growth phase.

A proper functioning photobioreactor system should be airtight and water tight. Thus, the preferred embodiment of the invention has the number of connections and fittings in the total system kept to a minimum preferably by extruding the photobioreactor on site in long sections. Preferably, such section may be 10-300 feet in length. Other methods of manufacturing may be employed such as molding the tubes.

The preferred embodiment of the invention may be fabricated from any material, including glass, but preferably a plastic that has the optical clarity to permit photosynthesis and can withstand long-term UV radiation exposure and exposure to corrosive saltwater, heat and cold, and expansion and contraction. Glass, and opaque or translucent plastics may also be used, as long they meet the needs of the photoautotrophic organisms to be grown in the system. Any person skilled in the art of thermoplastics can specifically design a plastic, or plastic mix which can be used for the photobioreactor tube. Virgin resins may be used to manufacture the tubes, but since cost is a likely significant factor, recycled plastics are preferred. A few of the particular plastics can include High Density Polyethylene (HDPE), Polyethylene Terephthalate (PET), acrylic, Lucite, polypropylene and polycarbonate. The location of the facility, the desired cost of the facility, the desire life-span of the photobioreactor are all factors that must be considered before deciding on the type of material to use.

Designs for photobioreactors in the prior art are intended for the production primarily of biomass, and secondarily of products derived from the biomass. They require inputs of carbon dioxide, water, mineral nutrients and light. They have outputs of oxygen and biomass. As a practical matter they may also have outputs into the growth medium, which must be separated from the biomass, water vapor, and incidental components of the gas phase such as nitrogen. Methods have been disclosed for the production of hydrogen using cultures of organisms in a photobioreactor designed and operated for that purpose. Hydrogen producing photobioreactors provide an anaerobic environment in which hydrogen production occurs. There may be internal production of biomass that is consumed as part of the hydrogen production process. The only essential output is hydrogen, and the only essential inputs are water and light. The ethanol producing photobioreactor system of the present invention has inputs of carbon dioxide and water and light. As a practical matter, it may be necessary to introduce some mineral nutrients into the reactor to allow enough growth for cell replacement, but addition of mineral nutrients is not inherent in the design of the process as it is in a biomass producing photobioreactor. The present methods of producing ethanol and other biofuels can be performed with a nutrient deficient growth medium.

Unlike the hydrogen producing photobioreactor, carbon dioxide is required. Furthermore, in contrast to a biomass producing photobioreactor, the ethanol producing photobioreactor of the present invention has outputs of oxygen and ethanol and does not require than the culture be harvested to recover any produced biofuel. As a practical matter, there may be some discharge of biomass from the photobioreactors of the present invention to prevent the development of cultures with excessive cell density, or to collect a test sample, but the production of the biomass is not a desired feature. Unlike the hydrogen producing photobioreactor, the ethanol producing photobioreactor does not produce hydrogen, but produces both oxygen and ethanol. Furthermore, while the ethanol producing photobioreactor of the present invention may be optimized to remove excess oxygen, it does not require anaerobic conditions as required by hydrogen photobioreactors.

Both hydrogen producing photobioreactors and biomass producing bioreactors are tolerant of heterotrophic contaminants that are not disease organisms. Some methods even call for the addition of heterotrophs. The hydrogen and biomass products are not susceptible to biological degradation. In contrast, ethanol is readily degraded by many heterotrophs in the presence of oxygen, so it is essential that such heterotrophs be excluded or their growth otherwise prevented in the ethanol producing photobioreactor. All liquid and gases entering the photobioreactors of the present invention can be sterilized using UV and/or filtration to reduce the possibility of contamination by foreign, unwanted microorganisms.

The overall size of photobioreactors and the number of photobioreactors used in conjunction with one another can vary greatly. Given the enormous scale required to manufacture industrially significant volumes of biofuels using photoautotrophic organisms, the dimensions of the photobioreactors should be large. A large biofuel facility will cover a thousand to many hundreds of thousands of acres. A preferred embodiment comprises a width of about 2 to about 3 feet for the photobioreactor is the average that would be optimal, but any size that incorporates the overall design aspects of the photobioreactor technology can be used. The overall width and height of the photobioreactors can be determined by evaluating a number of factors at the site of installation. The desired annual biofuels production volume, the desired cost and useful life of the facility, the physical terrain of the facility site, the solar exposure and the type of organisms that will be grown in the facility are all considered when designing photobioreactors for a particular location. A person skilled in the art of facility engineering can calculate the various cost/dimension relationship for the photobioreactor tubes. The tube photobioreactors should be as long as possible in order to minimize the number of connections in the system, which reduces the possibility of leaks that could lead to contamination. The tube photobioreactors can be constructed similar to the way conventional pipelines which require a completely enclosed airtight or liquid tight environment are constructed. Recent advancements in plastics extrusion technologies allow extrusion of large-diameter plastic structures of over 6 feet in diameter. Extruded plastic elements can make up the total structure of the photobioreactors. It is also possible to have an extruded lower part of the chamber made of rigid plastic and have the upper part of the chamber made of flexible plastic sheeting which is held in place by internal air pressure or supported by plastic or non-corrosive framing members at intervals. One can also manufacture the photobioreactor by molding, through any suitable molding technique available including blow molding or rotational molding or extruding, in one or more parts and where necessary, then joining the molded units together.

Preferably, little or no external energy is needed to operate the photobioreactors. In particular, it would be preferable if energy is not used to pump growth medium through the photobioreactors; however, in some instances it may be necessary to do so in order to provide churning and mixing to the growth medium, which ensures uniform exposure of cells to solar radiation and promotes gas exchange between the growth medium and the gas in the upper part of the chamber. Linear flow through solar tubes can reduce the overall photosynthesis since cells near the middle or bottom of the tubes receive less light than those towards the top. An embodiment hereof utilizes a flow of growth medium, preferably due to gravity, and internal static mixers such as internal baffles to provide appropriate mixing. These flow baffles are static in nature, thus requiring no additional energy input beyond the flow rate determined by the pumping system and gravity. The careful balancing of mixing in the tubes with creating turbulent flow is important, since the cells are sensitive to sheer damage during heavy mixing. The design of the photobioreactor in this embodiment mimics the mixing and churning in a natural stream lined with rocks. The turbulent flow in the photobioreactor not only provides the necessary mixing for maximal photosynthesis in high density cultures, but also serves to remove dissolved oxygen and enhances absorption of $CO_2$ from the air/$CO_2$ mixture in the controlled air head above the culture. This also helps to stabilize the culture pH and increases the resident time of the biomass in the photobioreactor for photosynthesis.

The photobioreactor can also be fitted with dams of varying heights that can be used to control the flow of the culture in areas where there is a greater natural slope. This permits steeper surfaces to be used for production facilities and lower overall installation costs. In a further embodiment, the dams can provide the amount of churning needed for cultures such as Synechococcus or Synechocystis which grow in high densities and need turbulence.

The dimensions of the photobioreactor provided herein can be varied to permit the mass culture of various genera of photoautotrophic organisms. In addition, the photobioreactor can accommodate different levels of growth medium to meet the needs of various organisms. Preferably, the growth medium has a depth between about 6 inches and 12 inches.

A further embodiment of this method of ethanol collection and removal is to pass the gas phase or a portion of the gas phase through a cold trap, which results in the removal of essentially all of the ethanol from the gas phase. This portion of the gas phase can then be vented to the air to allow for removal of excess oxygen, or the oxygen can be collected and used. Heat exchangers and the like can be used to reduce energy costs associated with cooling.

Although the present invention may be adapted to a vast number of overall physical configurations substantially similar to those shown in FIGS. 1-7, the concepts for growing genetically modified photoautotrophic organisms in a closed system on a massive scale for the production of biofuels remain the same. The present invention overcomes the well documented problems with open pond production systems, biomass growth and accumulation, as well as enables the cost effective construction of large capacity closed production systems. It will be understood by an ordinary person skilled in the art that the invention will not be limited to the specific designs and structures illustrated in the drawings.

FIG. 1 shows one photobioreactor of the present invention. The photobioreactor comprises an upper part of the chamber 1 and lower part of the chamber 2. Upper chamber 1 is at least partially translucent, preferably transparent. A temperature maintenance compartment 3 is located below the lower part of the chamber to cool or heat the growth medium 8. The photobioreactor may optionally have an interlocking tab 6 to secure the photobioreactor to an adjoining photobioreactor, or a securing tab 7 to fix the photobioreactor to a supporting surface. One or more supply inlets 5 add water, nutrients, carbon dioxide or any other necessary inputs to the system. Ethanol, or other biofuel, released by genetically enhanced organisms in the growth medium 8 evaporates into the headspace 9 in the upper part of the chamber 1 and condenses on the inner surface 10 of the upper part of the chamber 1.

Figure 2:
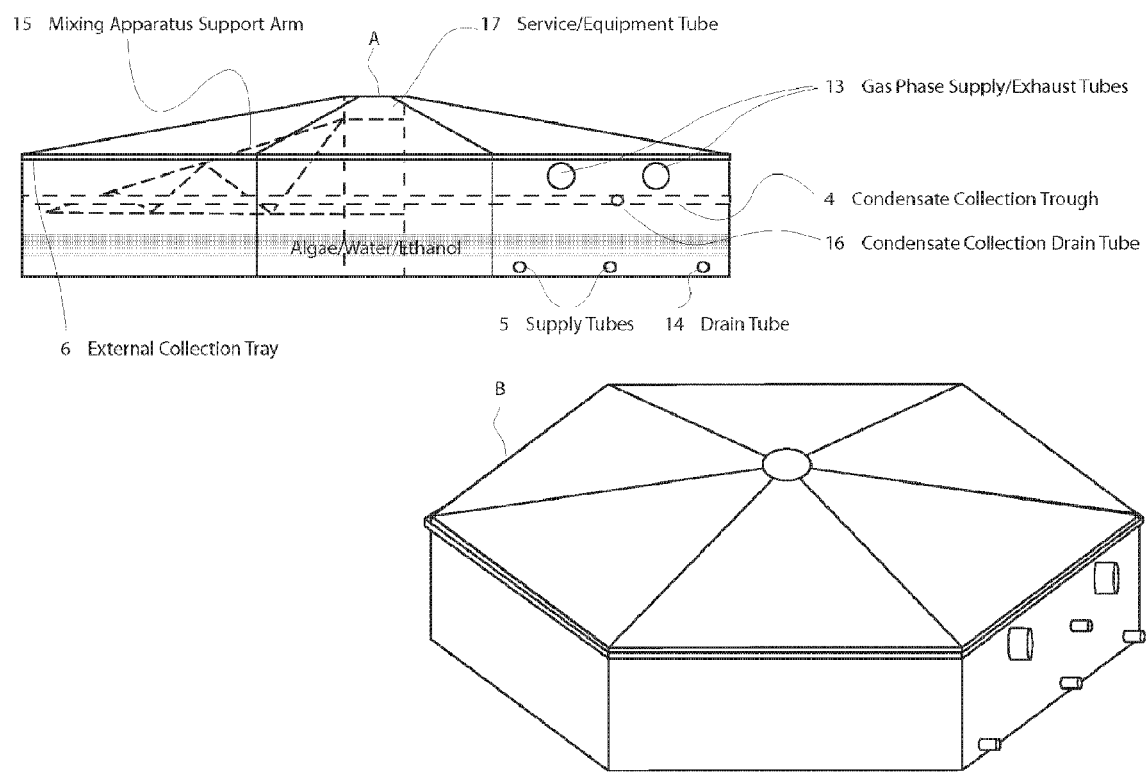
FIG. 2 shows a photobioreactor of the present invention having a hexagonal dome shape.

The photobioreactor depicted in FIG. 1 is in the shape of a rectangular tube; however other shapes and configurations are possible. FIG. 2 shows a photobioreactor in the shape of a hexagonal dome. The supply inlets 5 can be positioned near the bottom of the lower part or any other part of the chamber 2. Additionally, the photobioreactor may contain a drain tube 14, a mixing device 15 (in this embodiment an arm that is rotated around the photobioreactor) and a service tube 17 at the top of the upper part of the chamber 1 to provide access to the photobioreactor. The photobioreactor may also have condensate collection tube 16 connected to the collection trough 4 inside the upper part of the chamber 1, and gas outlets 13. The gas outlets 13 are used to remove gas from the upper part of the chamber 1 to a gas collection and separation apparatus (not shown) and can serve as an oxygen exhaust valve to vent excess oxygen out of the photobioreactor. FIG. 3 shows photobioreactors of the present invention also having different designs.

FIGS. 4A-4B show a photobioreactor similar to that depicted in FIG. 1 additionally containing multiple upper coolant compartments 18. The upper coolant compartments 18 in FIG. 4A extend across the upper part of the chamber 1 and separate the upper part of the chamber 1 into multiple portions. In addition to promoting condensation of the biofuel by cooling the gas 9 in the upper part of the chamber 1, the upper coolant compartments 18 provide increased inner surfaces 10 for condensation to occur. The upper coolant compartment 18 can also be positioned along the surface of the upper part of the chamber 1 as depicted in FIG. 4B.

Figure 5:
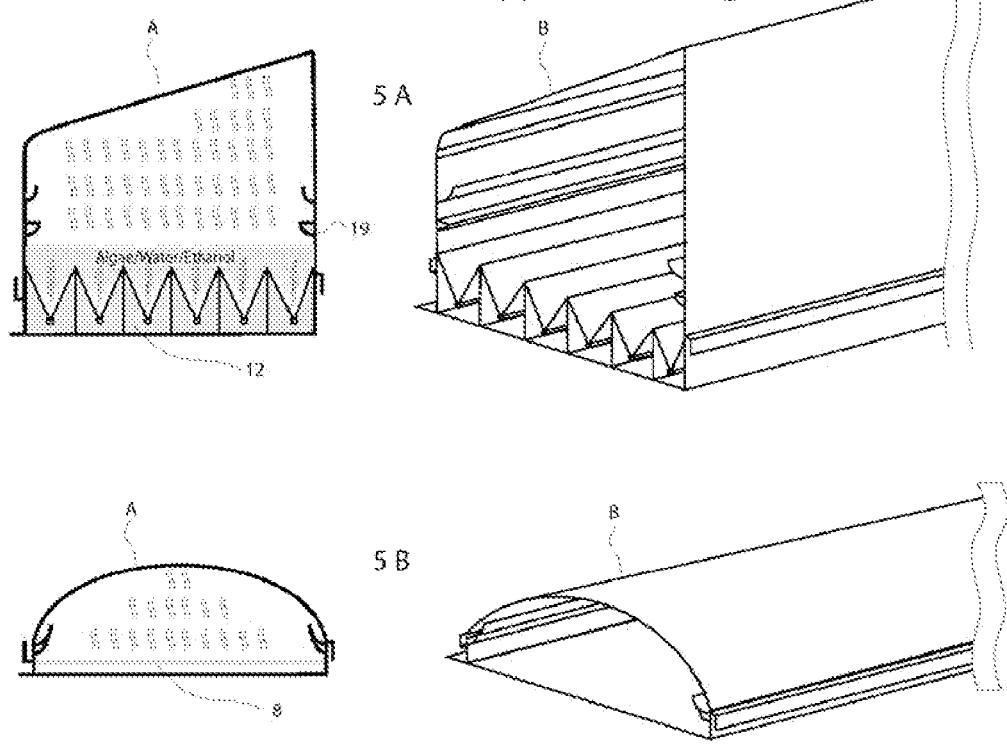
FIGS. 5A and 5B shows alternative tube designs of the photobioreactor similar to the photobioreactor of FIG. 1.
Figure 6:
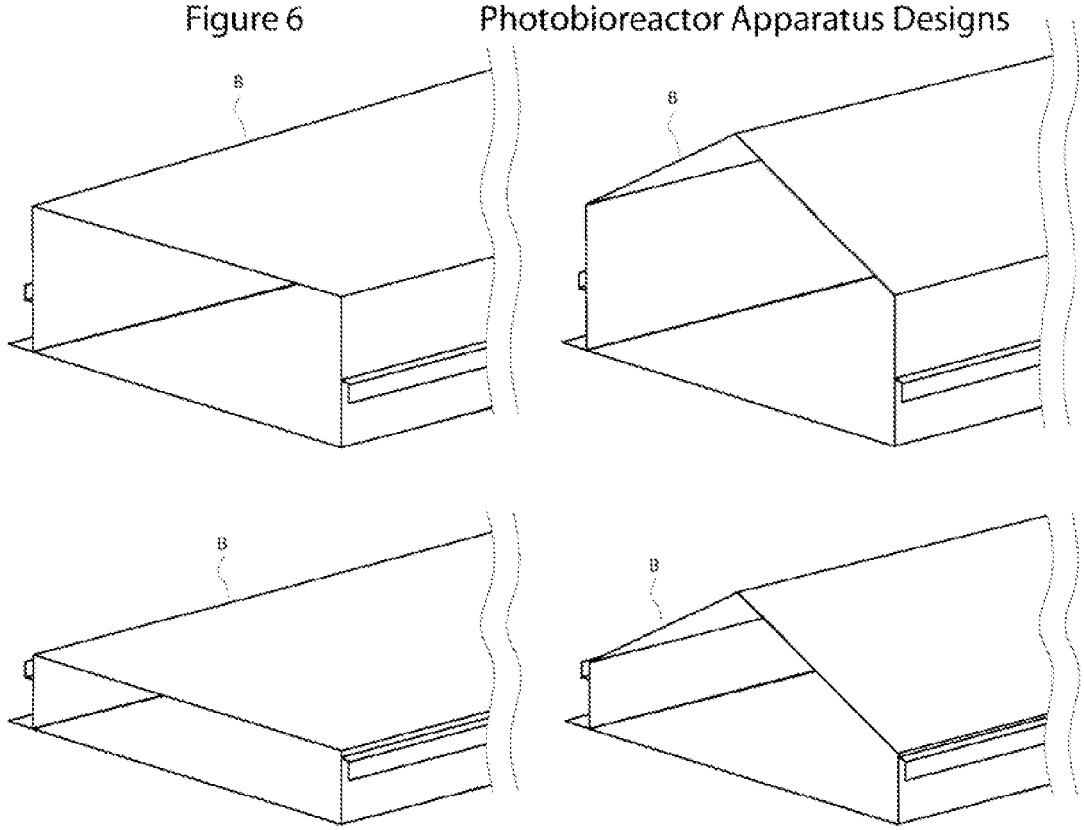

FIG. 5 illustrates additional shapes and designs similar to the photobioreactor of FIG. 1. The tube shape designs include circular tubes and other polygonal shapes. FIGS. 6 and 7 illustrate additional different designs of photobioreactor tubes suitable with the present invention.

Figure 8:
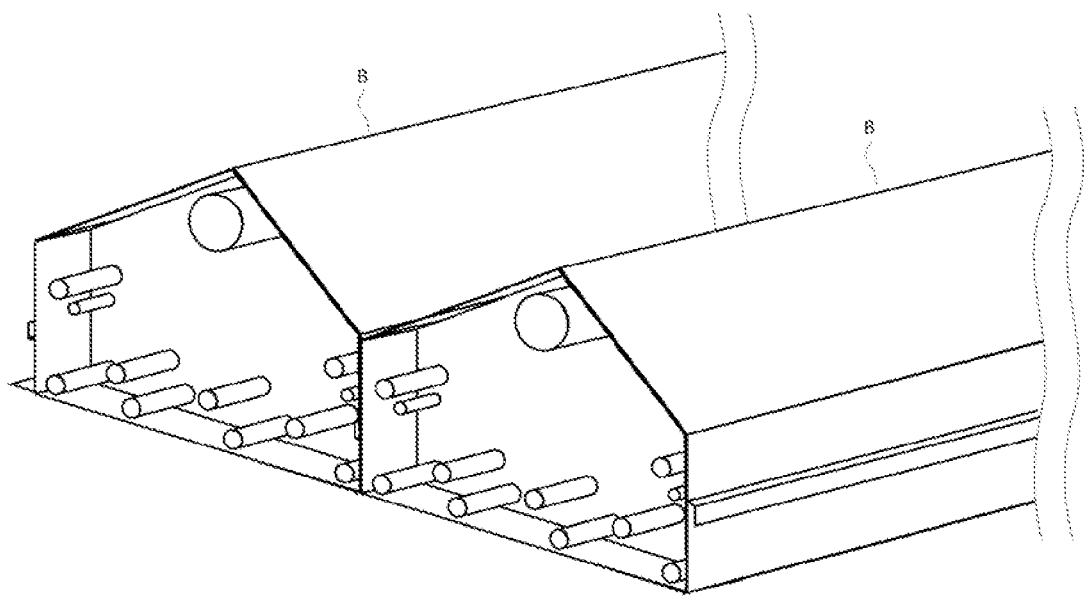
FIG. 8 shows a three-dimensional view of the ends of two photobioreactors placed adjacent to one another.
Figure 9:
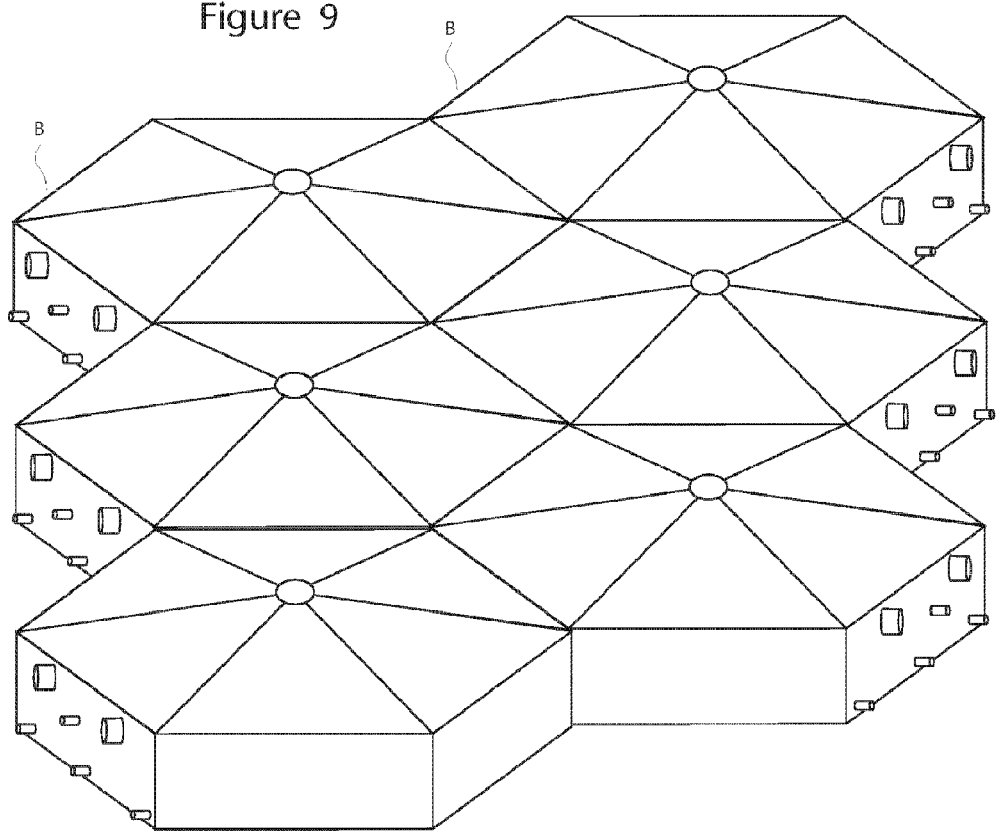
FIG. 9 shows hexagonal dome shaped photobioreactors fused together having multiple positions for gas and nutrient inlets and outlets.

In use, multiple photobioreactors can be placed next to one another FIG. 8 and FIG. 9 to maximize production of ethanol of another biofuel. FIG. 8 shows a three-dimensional end view of two photobioreactors of the present invention placed adjacent to one another. This configuration provides easy access to the supply inlets 5. The condensed ethanol is removed from the photobioreactor through condensate collection drain tubes 16, which are connected to the collection trough 4 (not shown). Alternatively, a photobioreactor system is designed as several photobioreactors fused together as shown in FIG. 9.

Figure 10:
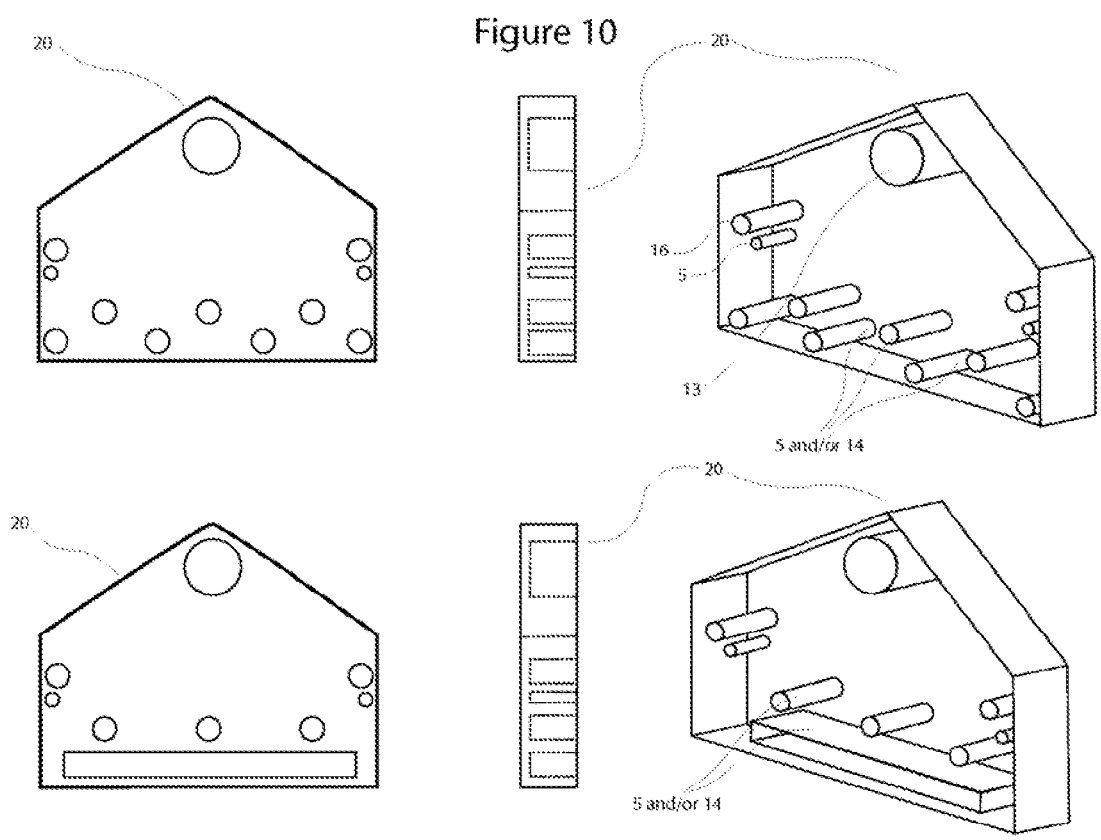
FIG. 10 shows a rear, cross-sectional and front view of end plugs used to seal the inlets and outlets of a photobioreactor similar to than shown in FIG. 1.
Figure 11:
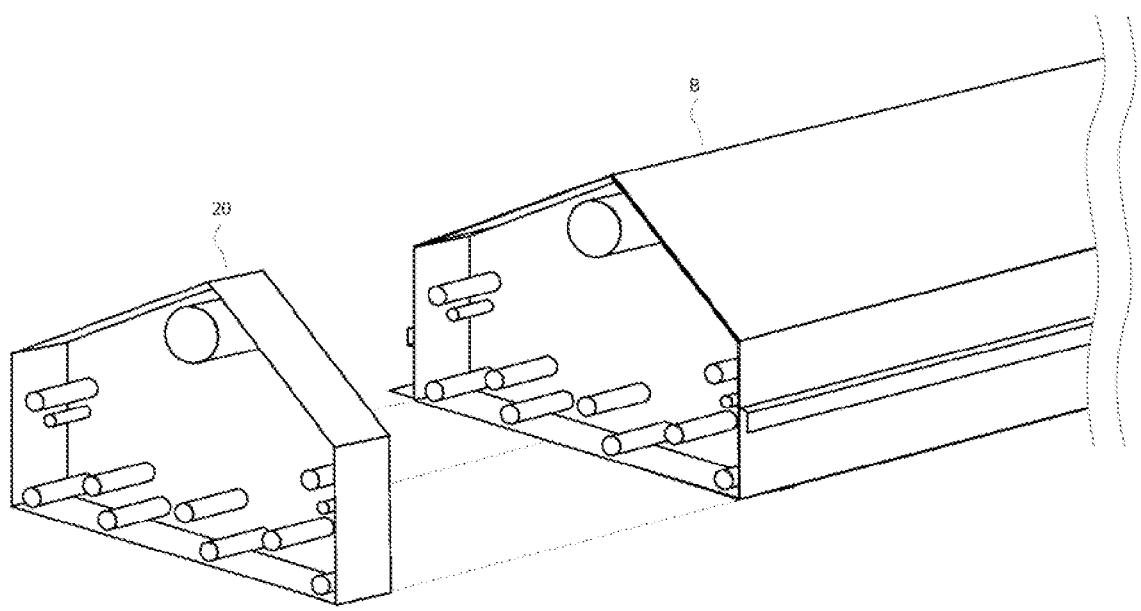
FIG. 11 shows a three-dimensional view of the end plug of FIG. 10 installed at the end of a tube shaped photobioreactor.

Both ends of a tube shaped photobioreactor may have inlet and outlet tubes, however, in some embodiments only one end may need to have inlets and outlets. FIG. 10 shows a rear view, side view, and front view of an end plug 20 that provides an air and watertight termination at the ends of photobioreactor. End plug 20 fits snugly into the ends, or alternately over the ends of the photobioreactor and provide connections to the supply inlets 5 and 19, drain tubes 14 and 16 and gas outlets 13. Also, caps can be installed over all inlets 5, 19 and outlets 13, 14 and 16 to seal off any fittings. End plugs 12 can be permanently sealed to the ends of photobioreactor or they can be held into place with various fastening systems and sealed. By not permanently sealing the end plug 12, access to the photobioreactor can be gained for repairs or cleaning. The connections can be of any size or shape that allow for the efficient exchange of air and inputs into the photobioreactor and can be straight pipe or threaded connections. The end plug 20 can be made as one single piece by molding or other acceptable means. End plugs 20 can be installed to a photobioreactor as shown in FIG. 11.

Figure 12:
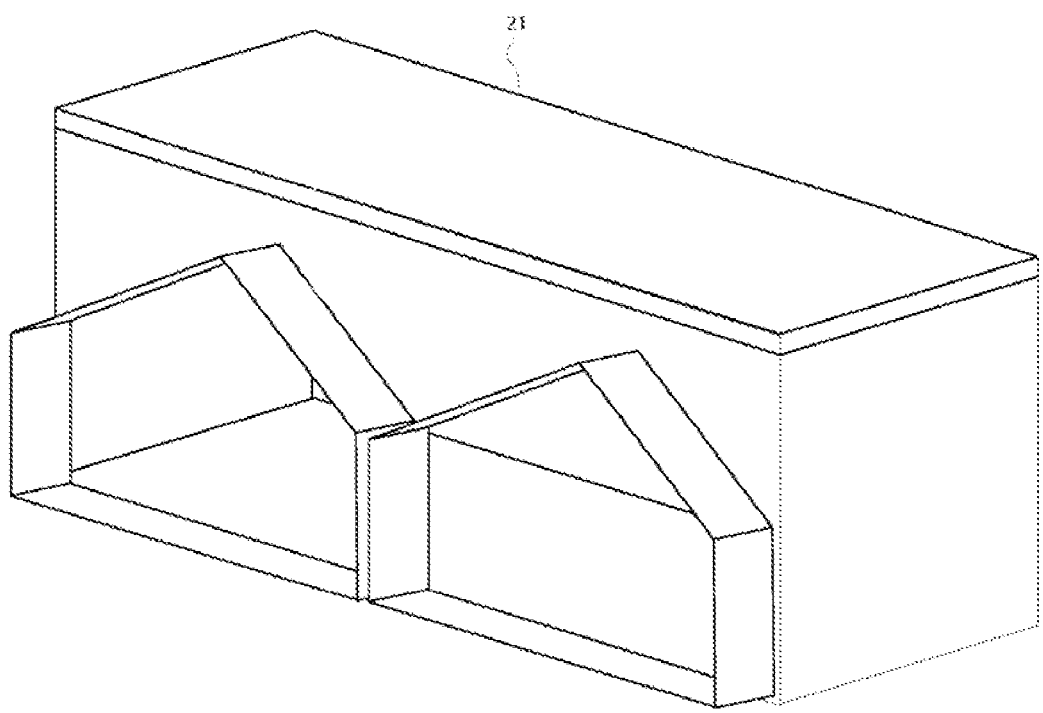
FIG. 12 shows a three-dimensional view of a photobioreactor flow connector unit that is used to join separate tube shaped photobioreactors.
Figure 13:
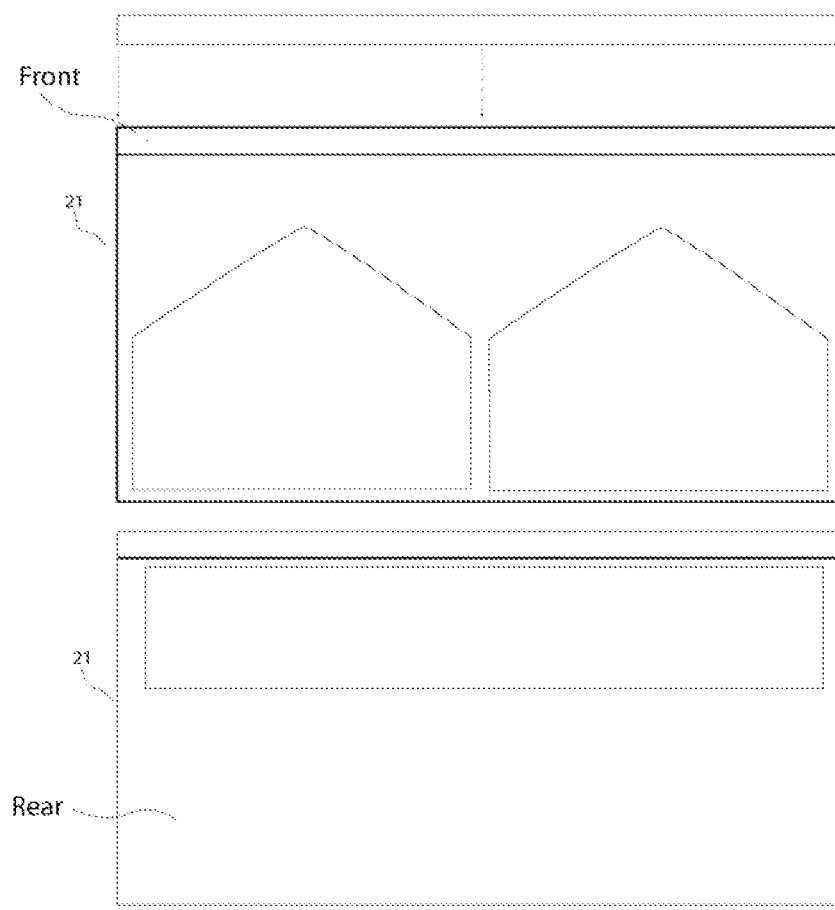
FIG. 13 shows a front and rear view of the flow connector unit of FIG. 12.

FIGS. 12 and 13 depict the front, rear and three-dimensional views of the photobioreactor flow connector 21. This flow connector 21 is used to connect to the ends of two separate photobioreactors to continue the flow in the joined tubes in the opposite direction. Flow connector 21 has openings on the top and on the back for access to the photobioreactor for cleaning and repair. Flow connector 21 is connected to the photobioreactors by inserting into the open ends of each and permanently sealing the photobioreactors with appropriate adhesives. The final design of flow connector 21 will be such that it will be able to join matching separate photobioreactors regardless of their final design.

Figure 15:
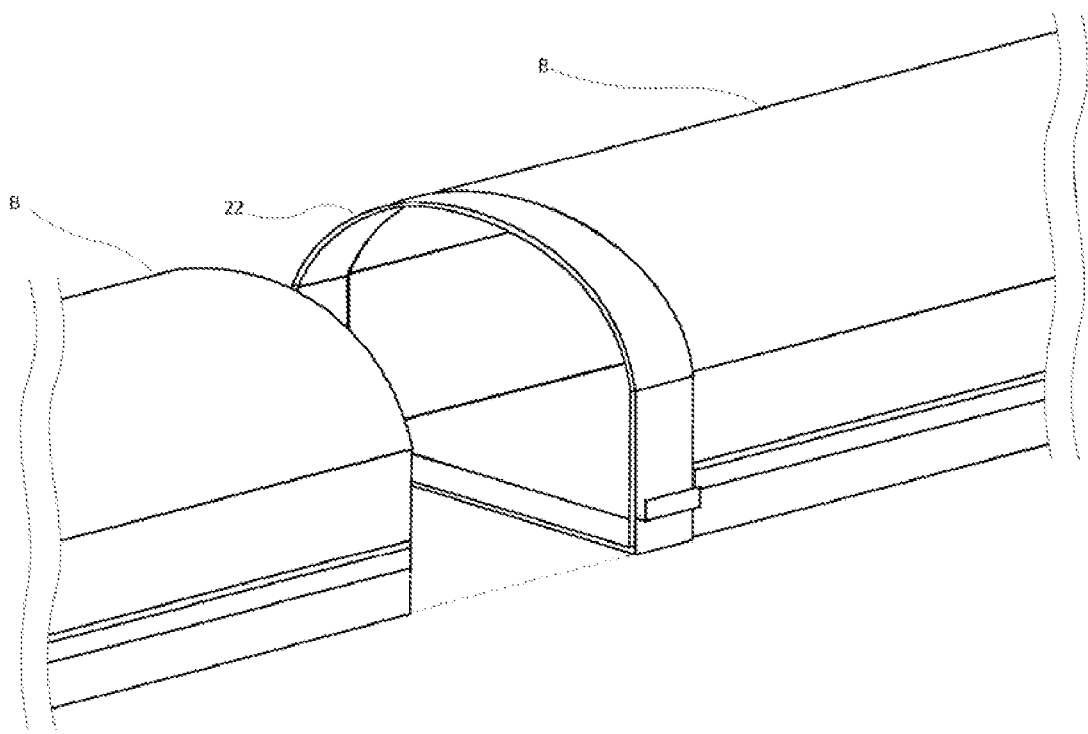
FIG. 15 shows a photobioreactor coupling unit installed on one photobioreactor ready to receive a second photobioreactor.
Figure 16:
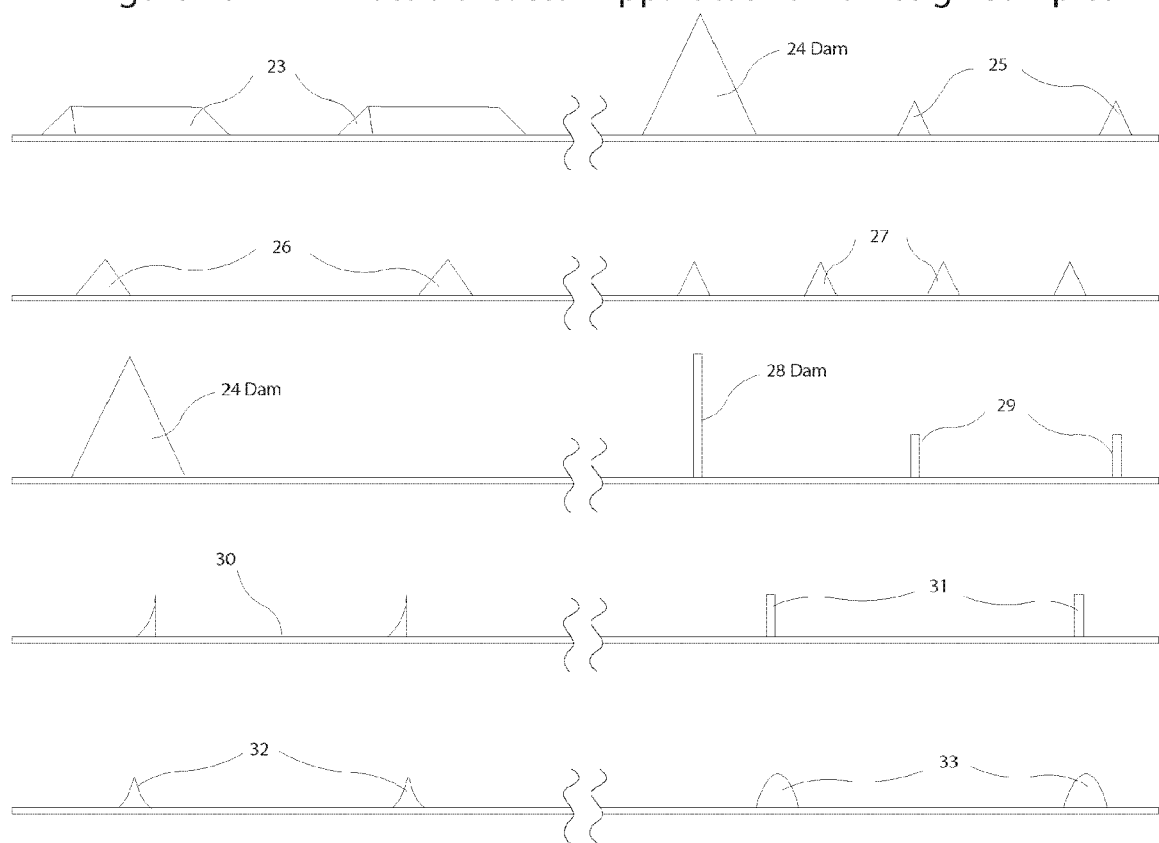
FIGS. 16-19 show the top and side views of various designs and configurations of flow dams and baffles placed at the bottom of a photobioreactor utilizing a pump or flow of liquid through the lower chamber.
Figure 17:
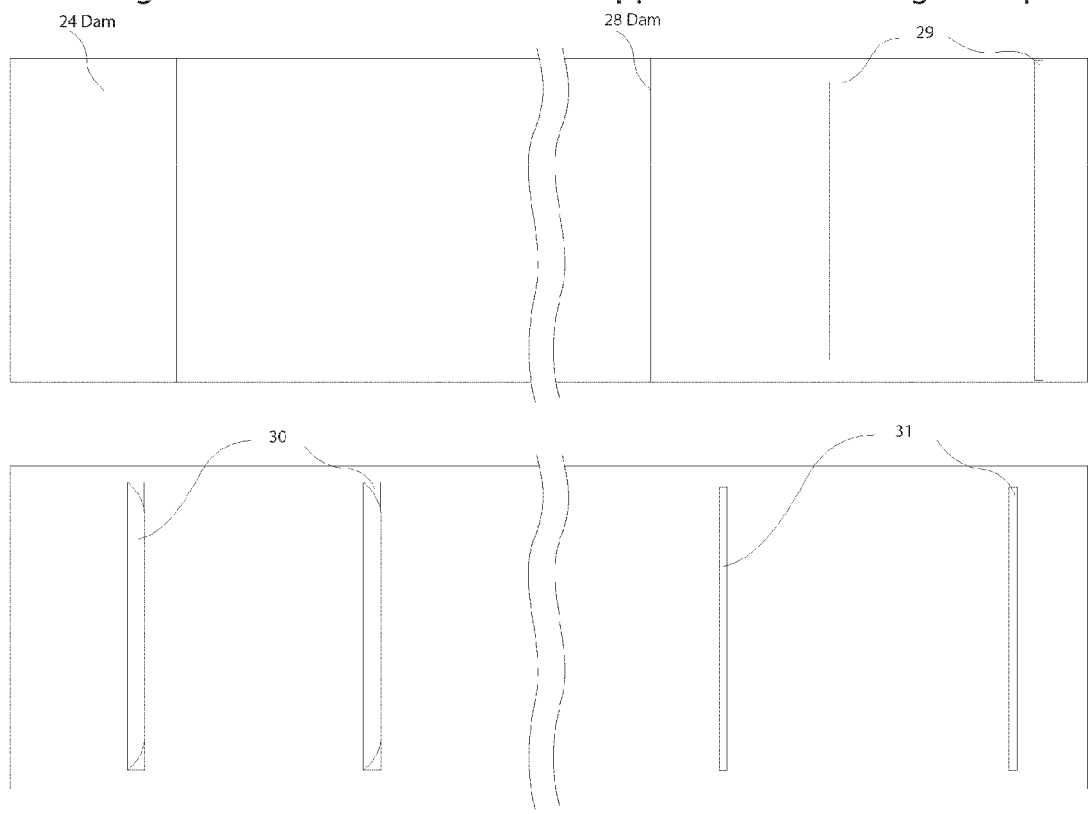
Figure 18:
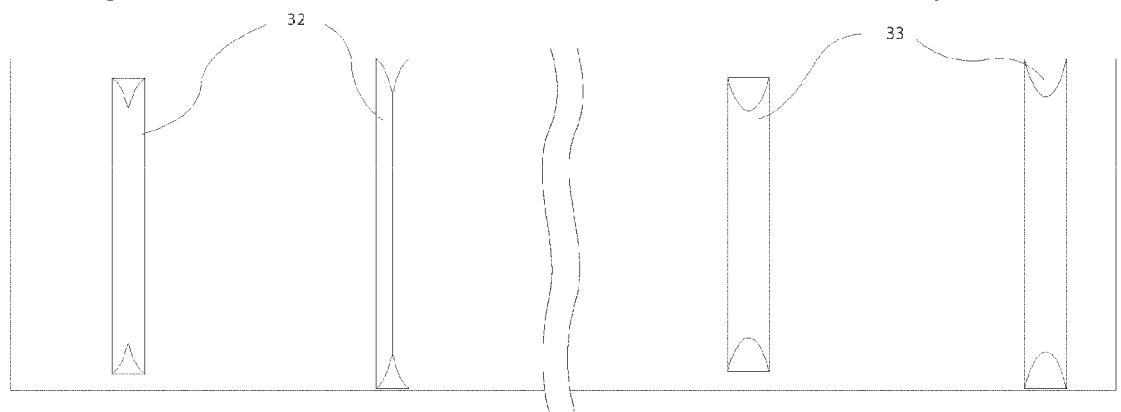
Figure 19:
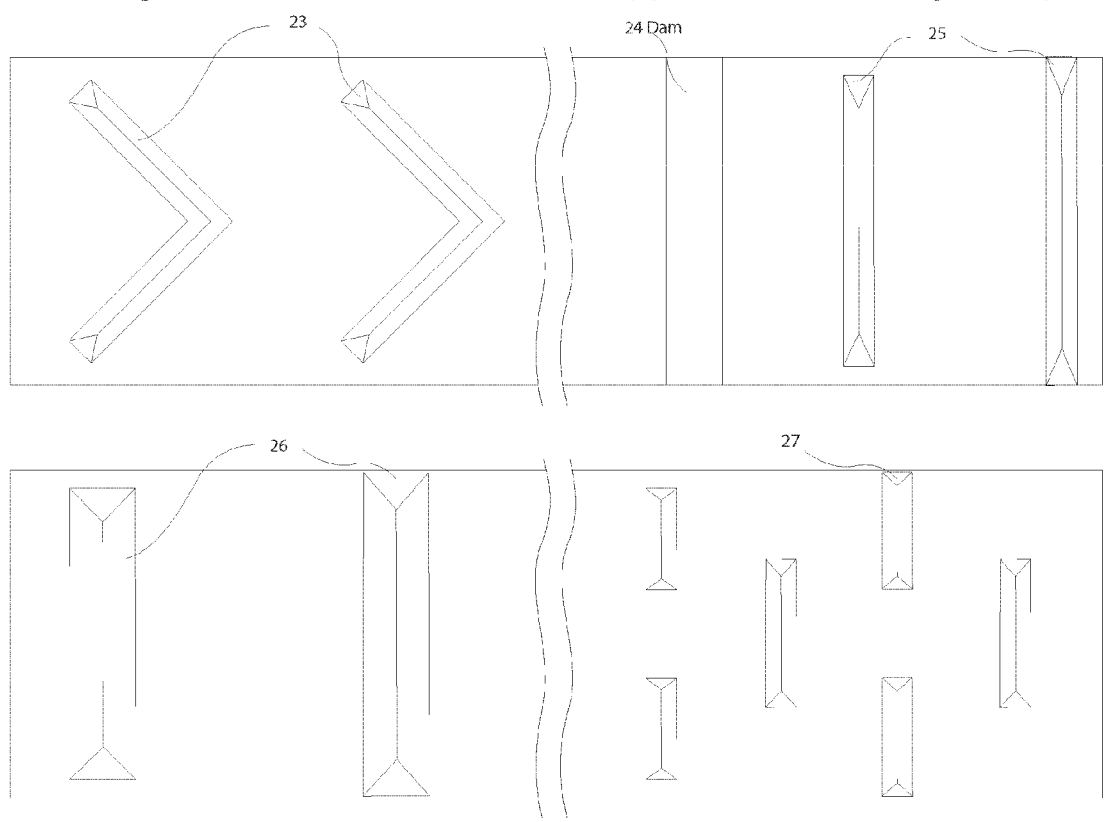

FIG. 14 depicts coupling unit 22 which is used to join a photobioreactor to another photobioreactor. FIG. 14 cross-section view shows the design of the coupling as well as how the coupling is attached to the photobioreactor. The couplings should be permanently attached to two separate photobioreactors using adhesives. The installed coupling unit 22 allows the connection of two short photobioreactor tubes into one longer tube. FIG. 15 shows a three-dimensional view of an installed photobioreactor coupling unit 22. The final design of coupling unit 28 will be such that it will be able to join matching separate photobioreactors regardless of their final design.

FIGS. 16-19 show various non-comprehensive configurations of the flow dams 24 and 28 and baffles 23, 25, 26, 27, 29, 30, 31, 32 and 33 pressed and/or molded into, or attached with adhesives to the inside bottom of the photobioreactor. FIGS. 16-19 do not embody all of the potential variations embodied in the invention.

Figure 20:
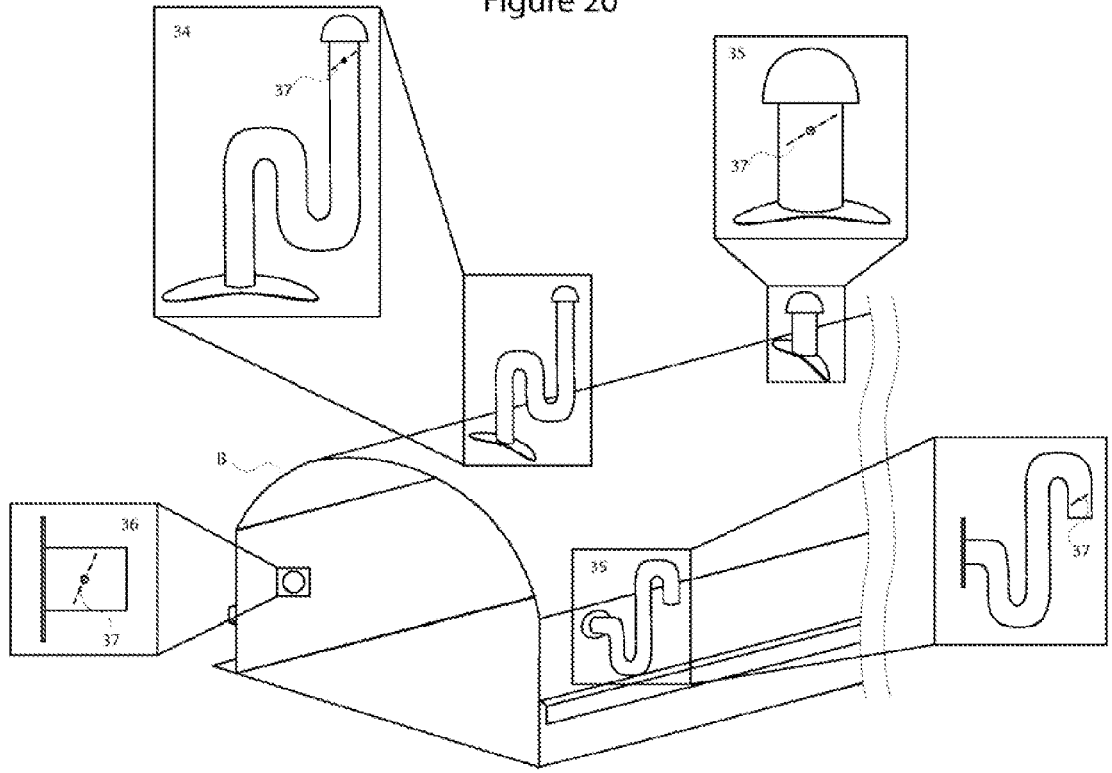
FIG. 20 shows a three-dimensional view of various tube fittings used to connect the inlet and outlet tubes for photobioreactors of the present invention.

FIG. 20 shows a three-dimensional view of various photobioreactor fittings. Various fittings 34, 35, 36 and 37 can be fixed to photobioreactor by cutting the appropriate size hole in the body of the bioreactor and attaching the fittings using adhesives, solvents or silicones. The fittings 34, 35, 36 and 37 can be used for venting of excess oxygen, addition or removal of various gases, nutrients, growth medium, water and buffers as well as for various probes and environmental monitoring devices. Each fitting can contain a valve 37, either electronic or manual, to control when the fitting is open or closed.

Figure 21:
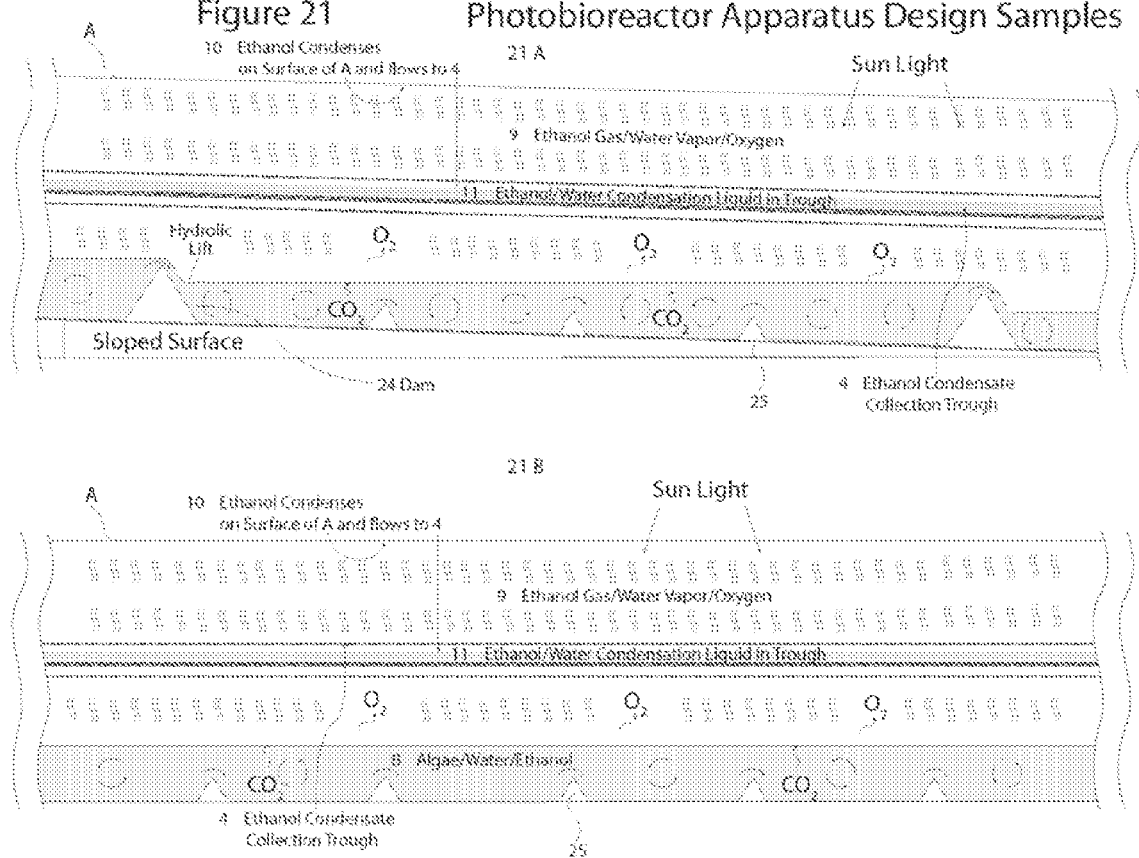
FIGS. 21A and 21B illustrate the turbulence and gas exchange in two photobioreactors having baffles and dams.

In situations where the growth medium is pumped or otherwise caused to flow through the photobioreactor, the present invention provides several features which provide an optimal environment for organism growth. In particular, mixing or churning ensures that the cells in the culture are more evenly exposed to sunlight, releases excess dissolved oxygen from the growth medium, and improves absorption of carbon dioxide. The photobioreactor shown in FIG. 21A is placed on a slope and utilizes gravity to transport the growth medium 8 through the lower part of the chamber 2. Alternatively, the growth medium 8 is pumped through the lower part of the chamber 2, as shown in FIG. 21B. As shown in FIGS. 21A and 21 B, the bottom surface of the lower part of the chamber 2 contains various integrated flow dams 24 and 28 and baffles 23, 25, 26, 27, 29, 30, 31 and 32 to provide significant churning in the growth medium 8. The flow dams 24 and 28 and baffles 23, 25, 26, 27, 29, 30, 31, 32 and 33 may also have the configurations depicted in FIGS. 16-19. These flow dams 24 and 28 and baffles 23, 25, 26, 27, 29, 30, 31 and 32 can be integrated into or attached to the bottom surface of the lower part of the chamber 2. A person skilled in the art of fluid dynamics can readily design the optimal configuration of the flow dams 24 and 28 and baffles 23, 25, 26, 27, 29, 30, 31 and 32 based on the variables of the plant location and needs of the organisms.

Figure 22:
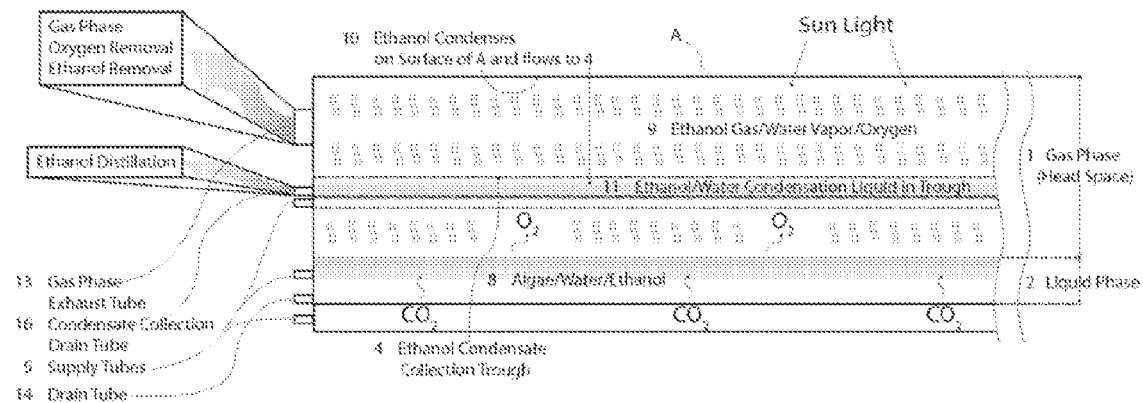
FIGS. 22A and 22B illustrate the gas exchange above and below the growth medium and different phases of ethanol in a photobioreactor.
Figure 23:
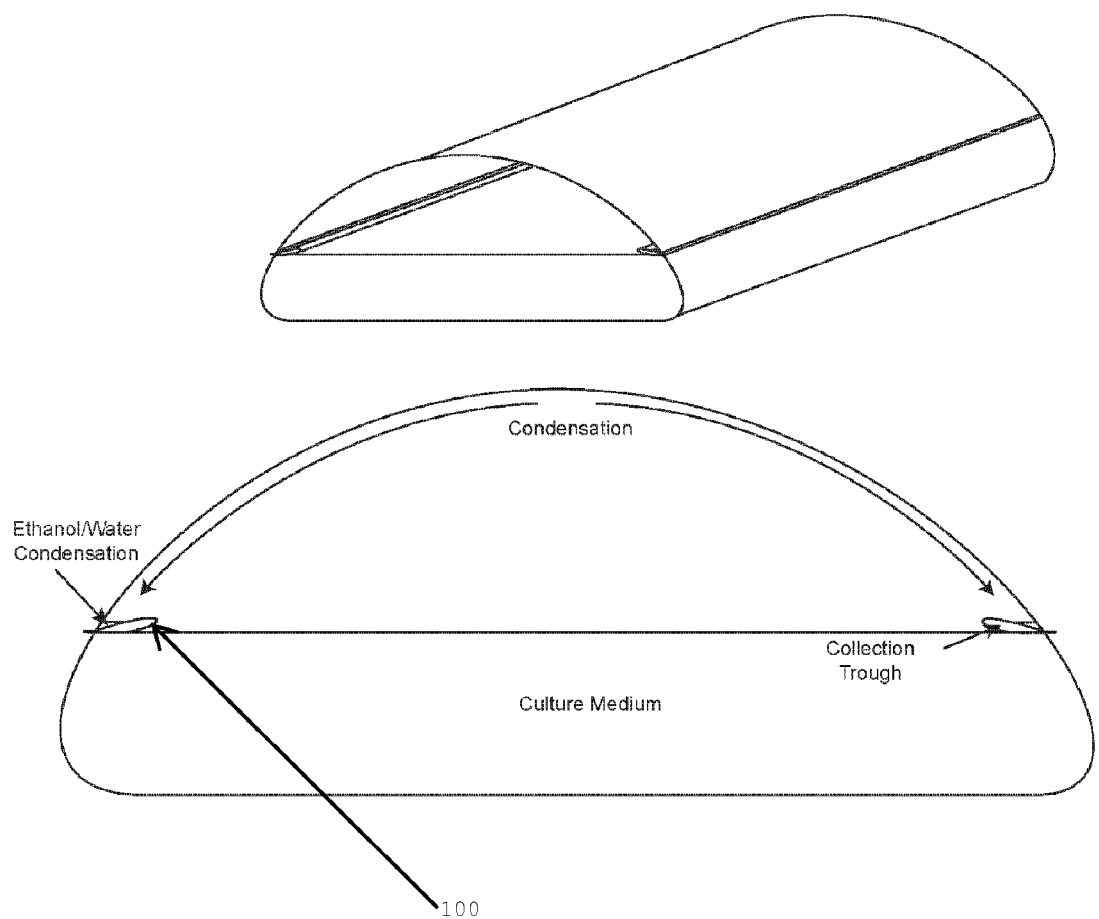
FIG. 23 illustrates a photobioreactor made of tubular polyethylene material with condensate collection troughs manufactured into the final photobioreactor.

As illustrated in FIG. 22, sunlight enters through the top of the upper part of the chamber 1. Algae in the growth medium 8 uses the sunlight to produce and release ethanol into the growth medium where it is evaporated 9 into the upper part of the chamber 1. The gas 9 in the upper part of the chamber will include oxygen, evaporated water and ethanol. Ethanol will condense on the inner surface 10 of the upper part of the chamber 1, and the condensate 11 will collect into the condensate collection trough 4. As depicted in FIG. 22, carbon dioxide is provided to the growth medium 8 as a gas present in the lower part of the chamber 1. Thus, the growth medium 8 absorbs carbon dioxide and releases oxygen into the upper part of the chamber 1. Various inlets 5 and 19 supply the necessary inputs into the system and outlets remove 13, 14 and 16 remove gases, liquid and biomass from the system.

The biological processes in the present invention do not produce ethanol in the presence of water and other materials or other biofuel product. Rather, the product must be purified to separate it from water, and possibly other cellular products and contaminants. Therefore an additional aspect of the production of ethanol with a photobioreactor is the purification of ethanol or other biofuels. The biofuel product can be purified from the gas phase of the photobioreactor as well as from the condensates. The elimination of oxygen from a biomass producing photobioreactor is generally accomplished by venting a gas phase enriched in oxygen to the atmosphere. While this same method can be used with the present invention, the oxygen stream will contain the biofuel product and may substantially reduce the productivity of the photobioreactor unless measures are taken to prevent excessive product loss. Therefore another aspect of the present invention is the control of biofuel loss, particularly ethanol loss, in the oxygen exhaust stream.

The condensate can be removed as a liquid and purified by any known means, such as distillation, pervaporation, dephlegmation, etc., and may be further dehydrated by any known means such as zeolite dehydration or membrane dehydration.

Integration of Oxygen Exhaust and Ethanol Harvest Processes

The removal of a substantial amount of ethanol in the gas phase is unavoidable due to the requirements for oxygen removal. At a minimum, it is necessary to avoid losing too much ethanol as a consequence of oxygen release. Ethanol retention during oxygen release is a separation process, and it may be that the release of oxygen and the separation of ethanol from the vapor stream can be combined into a single operation that is more cost effective than independent operations would be. For example, the gas phase from the photobioreactor could be pumped past an oxygen permeable membrane at an elevated pressure and allowed to equilibrate with air through the membrane. The partial pressure of oxygen in the output gas from such a system would be over 21 kPa by an amount dependent on how closely equilibrium is approached. The remainder of the vapor phase would be ethanol and water. The vapor phase could further be passed through a dephlegmator to remove most of the water, and through a dehydration system to remove most of the remaining water.

Exclusion of Heterotrophs

Because ethanol is not always stable to biological degradation in the presence of oxygen, it is important to exclude, inhibit or kill heterotrophic organisms so that degradation of ethanol by heterotrophs is minimal. Methods for sterilization of equipment, solutions and gasses are well known to those skilled in the art, as is the preparation and maintenance of cyanobacterial or algal cultures which are axenic, that is, that contain no organisms of any kind other than the cyanobacterial or algal strain being cultured. Chemical treatments such as antibiotics are also well known, as are techniques for making cell lines of cyanobacteria or algae that are resistant to particular antibiotics. Antibiotics may be added to the cultures in the photobioreactors to eliminate any heterotrophic organisms present in the culture or as a prophylactic measure against potential infection. Additional methods for the control of heterotrophs as known in the art may also prove effective. The preferred embodiment of the invention is that the cyanobacteria or algae organisms themselves produce ethanol in the photobioreactor and when this level is near or above 5% in the culture, the ethanol itself will kill heterotrophs and assist in keeping the culture stable and near sterile.

Having now fully described the photobioreactors and methods provided herein in some detail by way of illustration and examples for purposes of clarity of understanding, it will be obvious to one of ordinary skill in the art that the modifying or changing the photobioreactor configurations and methods to utilize equivalent conditions, elements, steps, and other parameters is within the scope of the appended claims.

One of ordinary skill in the art will appreciate that starting materials, substrates, device elements, analytical methods, mixtures and combinations of components other than those specifically exemplified can be employed in the practice of the invention without resort to undue experimentation. All art-known functional equivalents, of any such materials and methods are included in the devices and methods disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the claims. Thus, it should be understood that although the photobioreactors and methods provided herein have been specifically disclosed in terms of embodiments, optional features, modifications and variation of the concepts herein disclosed can be utilized by those skilled in the art, and such modifications and variations are considered to be within the scope of the appended claims.

As used herein, "comprising" is synonymous with "including," or "containing," and is inclusive or open-ended and does not exclude additional, unrecited elements or method steps.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of analysis, additional biological materials, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application were specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art.

The meaning of terms includes text as follows.

The term "closed from the outside environment" includes the meaning that bacteria outside of the photobioreactor are restricted from entering into the photobioreactor and that ethanol formed within the photobioreactor is restricted from leaving the photobioreactor other than in predesigned ways.

The term "chamber" includes the meaning of the body of the photobioreactor which comprises an aqueous growth medium comprising a culture of genetically enhanced organisms disposed in the growth medium, wherein said organisms are selected from the group consisting of algae and cyanobacteria and a means to furnish sunlight to the organisms.

There is an upper part of the chamber which comprises a translucent or clear region to allow in sunlight. There is a lower part of the chamber which comprises an aqueous growth medium. The chamber encloses a gas-phase volume or head space. The chamber encloses a liquid-phase volume which comprises the aqueous growth medium. There is an inner surface of the upper part of the chamber upon which gas-phase water and ethanol can condense. The meaning of the term chamber may also be understood from the Figures.

The term "upper part of the chamber" or "upper chamber" comprises the region of the chamber which is translucent or clear.

The term "lower part of the chamber" or "lower chamber" comprises the region of the chamber comprising the aqueous growth medium. No physical barriers between the upper parts of the chamber and the lower parts of the chamber are required.

The term "continued daily basis" includes the meaning of the operation of the photobioreactor and refers to the continued production of ethanol from carbon dioxide by the organisms during the continued times for which sufficient light is available. The term "continued daily basis" further includes the meaning that ethanol can be formed day after day provided that there is sufficient light, carbon dioxide and nutrients present. The term "continued daily basis" further includes the meaning that the production of ethanol will be influenced by the weather, including the presence or absence of sun or clouds, and by the need to include nutrients, promoters, and carbon dioxide in the chamber, and by routine maintenance requirements, including the need to replace biomass and/or components of the photobioreactor.

The term "inner surface of the upper part of the chamber" includes the inner portion of the chamber upon which gas-phase ethanol and water condense to the liquid phase.

The term "inner surface of the upper part of the chamber" includes the inner portion of the chamber upon which gas-phase ethanol and water condense to the liquid phase.

The term "inlet and outlet tubes" refers to tubes connected to openings in the chamber of the photobioreactor.

The term "coolant compartments" refers to compartments that hold material that may be used to cool the chamber of the photobioreactor.

The term "mixing device" refers to any device that may be used to mix or stir the contents of the aqueous growth medium.

The term "measuring devices" refers to devices that may make measurements of parameters related to the photobioreactor and includes devices to measure temperature, pressure, and the amount of carbon dioxide, carbonate, salt, hydrogen ion, water, ethanol, oxygen and nutrient levels of the growth medium.

The term "treatment of the inside of the upper part of the chamber" includes any chemical or physical treatment of the surface of the inside of the upper part of the chamber of the photobioreactor which can affect the condensation of gas phase ethanol.

The term "additive, coating and physical modifications" includes any chemical or physical modifications of the chamber of the photobioreactor that can affect the photosynthesis reaction or the condensation of ethanol or water inside the chamber. Additives can include UV blocking agent, UV stabilizing agent, UV blocking coating, UV blocking film, an additive for stabilizing the plastic material, and agents for stabilizing the plastic material.

The term "closed reaction volume" includes the meaning that the volume defined by chamber of the photobioreactor is restricted to the entry of entities detrimental to the photosynthetic reaction and restricted as to the departure of ethanol from the reaction volume. The term "closed reaction volume" does not indicate that oxygen does not leave the reaction volume or that ethanol does not leave the reaction volume.

The term "liquid phase" includes both the liquid in the culture, and the liquid as a condensate, and includes both H2O and ethanol liquids.

The term "modular plastic extrusions, mounted on soil" includes the meaning of a plurality of photobioreactor units, comprising modular plastic, mounted on soil.

The term "means of temperature regulating the aqueous growth medium" refers to a means of temperature regulation which includes structures which regulate temperature through variation of light input or variation of temperature by input of heated or cooled fluids. The temperature of the aqueous growth medium can be regulated by electric heaters or thermal contact with heated or cooled fluids.

The means of introducing fluids and gases could include a nozzle, a valve, and venturi connected to a source of $CO_2$ which could include flue gas from a power plant of $CO_2$ from a cylinder The means of introducing carbon dioxide can include introduction through a tube from a $CO_2$ cylinder or from combustion gases of a fossil fuel combustion unit.

The means of converting the carbon dioxide into ethanol include photosynthetic processes involving microorganisms selected from the group consisting of genetically enhanced algae and cyanobacteria. Genetically enhanced algae and cyanobacteria (as described for example in U.S. Pat. No. 6,699,696) convert carbon dioxide into ethanol.

The means of separating ethanol from the liquid phase include a structure which allows for evaporation of ethanol from an aqueous growth medium into a headspace and subsequent condensation onto the surface of a chamber. The structure may include a semipermeable membrane.

An important discovery of this invention is that for photobioreactors of this invention is that solar evaporation allows for an enhancement in ethanol concentration. For a given concentration X of ethanol in the liquid-phase including the microorganisms we have data suggesting that the condensate formed by solar evaporation of the same liquid-phase is greater than X. This is based on data for the evaporation of ethanol and water from a liquid of ethanol and water in a prototype photobioreactor as illustrated below, with the data denoted ("Photobioreactor") corresponding to liquid in the lower part of the bioreactor chamber ("Pond") and with the data denoted ("Condensate") corresponding to the "evaporated then condensed" liquid. Photobioreactor Apparatus #5 and Photobioreactor Apparatus #6 are two example photobioreactors which embody the invention illustrate the enrichment or enhanced ethanol concentration.

Data for Photobioreactor Apparatus #5

| Day | Sample From | Ethanol concentration (mM) | Sample volume (L) | Ethanol in sample (mmol) |
|---|---|---|---|---|
| 1 | Pond | 224.04 | | |
| 1 | Condensate | 279.23 | 1.48 | 411.87 |
| 2 | Pond | 224.99 | | |
| 2 | Condensate | 275.83 | 2.00 | 551.67 |
| 3 | Pond | 222.37 | | |
| 3 | Condensate | 254.80 | 0.98 | 248.43 |
| 6 | Pond | 221.61 | | |
| 6 | Condensate | 256.30 | 4.10 | 1050.82 |
| 7 | Pond | 215.26 | | |
| 7 | Condensate | 273.83 | 0.90 | 246.45 |
| 8 | Pond | 212.93 | | |
| 8 | Condensate | 247.37 | 1.28 | 315.39 |
| 9 | Pond | 216.86 | | |
| 9 | Condensate | 253.06 | 0.73 | 183.47 |
| 10 | Pond | 253.93 | | |
| 10 | Condensate | 210.78 | 1.30 | 274.01 |
| 13 | Condensate | 169.57 | 3.80 | 644.37 |
| 14 | Condensate | 158.60 | 1.50 | 237.90 |
| 15 | Pond | 132.35 | | |
| 15 | Condensate | 166.46 | 1.43 | 237.21 |
| Sum of condensate | | | 19.48 | 4401.60 |

The ethanol yield in the condensate is 4.4 moles=203 g. Over 15 days the yield is 13.5 g/day, which for the active surface area of 1.42 m2 is 9.5 g/(d-m2).

The enrichment in ethanol, condensate/pond, for day 1 is 1.25.

Data for Photobioreactor Apparatus #6

| 1 | Pond | 230.84 | | |
|---|---|---|---|---|
| 1 | Condensate | 289.87 | 1.225 | 355.1 |
| 2 | Pond | 231.89 | | |
| 2 | Condensate | 292.67 | 1.6 | 468.3 |
| 3 | Pond | 227.12 | | |
| 3 | Condensate | 267.81 | 0.675 | 180.8 |
| 6 | Pond | 228.27 | | |
| 6 | Condensate | 270.83 | 3.725 | 695.6 |
| 7 | Pond | 225.92 | | |
| 7 | Condensate | 273.39 | 0.75 | 205.0 |
| 8 | Pond | 229.38 | | |
| 8 | Condensate | 273.83 | 1.1 | 301.2 |

-continued

| | | | | |
|---|---|---|---|---|
| 9 | Pond | 232.04 | | |
| 9 | Condensate | 280.41 | 0.575 | 161.2 |
| 10 | Pond | 233.75 | | |
| 10 | Condensate | 272.41 | 1.175 | 320.1 |
| 13 | Condensate | 186.75 | 2.9 | 541.6 |
| 14 | Condensate | 197.80 | 1.225 | 242.3 |
| 15 | Pond | 159.70 | | |
| 15 | Condensate | 192.10 | 1.2 | 230.5 |
| Sum of condensate | | | 16.15 | 3701.8 |

In a different reactor, an experiment was done with an ethanol solution at an initial level of 0.5% (v/v). The water phase comprised salt. Specifically, seawater was added to the reactor to an original depth of ~15.24 cm (6 in). The liquid volume was about 50 liters. The initial salinity of the water was 35 ppt. In this case, the ratio of ethanol concentration for condensate/pond was of the order of 3, higher than the 1.25 mentioned above. Salt is believed beneficial to enhanced ratios of ethanol/water in the condensate. In a working photobioreactor, the level of salt must be compatible with the functioning of the ethanol-producing cyanobacteria. In a working photobioreactor, the temperature must be compatible with the functioning of the ethanol-producing cyanobacteria. A preferred temperature range is 20 degree Celsius to 60 degree Celsius.

Example of a Flexible Tube Bioreactor

We constructed a 4.45'×50' tube photobioreactor with condensate collection troughs.

We special ordered (AT Films, Inc., Edmonton, Alberta) 10,000 pounds of high-density polyethylene (HDPE) 6 mil tubular film 43.7 inch diameter that was UV stabilized to last 4 years and included an anti-fog additive. The anti-fog additive reduces the light blocking of condensate collected on the surface of the photobioreactor from ~20% to ~4%. The tubular film was delivered on 500' rolls, and the film has a lay flat width of 5.708'. Starting with 50 feet of 6 mil tubular film laid flat on a long table we marked two lines the length of the tube 2.75" in from each edge.

This is our proposed water line when the photobioreactor is built. The final shape of the tube photobioreactor can be calculated by a person skilled in the art of mechanical engineering. We wanted our final photobioreactor tube width to be ~53" with 8" of water. Our mechanical engineer provided the shape of the photobioreactor tube (see figure) and the location of the waterline.

We start on one side of the tube and pushed in a fold "finger" to the inside of the tube (see figure). We adjusted the length of the finger to the final desired width of the collection trough 3". We folded this finger to the inside of the tube the whole length of the tube. We made sure the fold is even with the water line mark on the bag. We used three long pieces (aluminum—20'×1.74"×1.75") of angle iron to clamp the tube to the edge of the table, so 0.5" of the finger fold is hanging over the edge of the table and is held in place with the angle irons which are clamped on each end.

This is to hold the fold and the tube firm so the heat sealer can be run down the length of the tube without the tube moving. This "tongue" is 4 layers of the 6 mil tube with the water line mark about 0.5" from the edge of the table. Using a Bosch HS-CII portable/tabletop compact continuous band sealer (BaggingGuys.com) with the heat setting on 3.5 (~400 F), we sealed the finger the length of the tube.

We repeated this on the other side of the tube. The circumference of the finished tube was 124". We special ordered two fiberglass (Riley Composites, Inc., West Palm Beach, Fla.) end caps which will fit inside the tube to provide a means to seal the end and support the tubing fittings for water and air inlets/outlets (whatever size is desired, we used 0.5" BKF124, Aquatic Ecosystems, Inc., Apopka, Fla.).

The end caps have a shape like the tube reactor will have when it has the desired water level (8") and air pressure (0.6 psi). We marked the depth of the end cap from each end of the tube. We marked a point 4" from the inside of the end cap above the condensate collection trough. With a 0.5" hole saw, we cut a 0.5" round hole through the plastic and installed a 0.5" bulkhead fitting (0.5" BKF124, Aquatic Ecosystems, Inc., Apopka, Fla.) with gasket. We did this on one end of the tube (the expected downslope side, if the final installation has a slope. If no slope is expected, then either or both ends can have the outlets).

We then installed 0.5" FIPT/⅜" barbed nylon elbows (The Home Depot) in the outside of the bulkhead fittings. With a 0.5" hole saw, we cut two 0.5" round holes through the end cap, one above the water line and one below the waterline and installed 0.5" bulkhead fitting (0.5" BKF124, Aquatic Ecosystems, Inc., Apopka, Fla.) with gasket. We then installed 0.5" FIPT/FIPT nipples (The Home Depot) in the outside of the bulkhead fittings and attached plastic 0.5" FIPT/FIPT ball valves to the nipples. We then installed a ½"×³⁄₁₆" butyl tape gasket (Glue Products, Inc., West Palm Beach, Fla.) around the end cap and pulled the tube over the gasket.

We pressed the tube to the gasket. We used a ½" Manual Combination Strapping Tool and ½" Machine Grade Polypropylene Strapping (GlobalIndustrial.com) to apply a strap around the outside of the end cap over the tube and butyl tape and applied sufficient torque to squish the butyl tape to create a seal between the end cap and the tube.

At the opposite end of the bioreactor, we stuck a compressed air line in the open end of the fingers, and pumped compressed air into the inside of the finger for floatation 100. We completed the same sealing process on this end. The completed tube was filled with water to the bottom of the condensate collection troughs and air was pumped into the tube until it was taught. Inside the completed tube the water evaporates and condenses on the upper inner surface of the photobioreactor, flowing to the condensate collection trough.

Once in the condensate collection trough, the water flows down the trough via gravity and out the bulkhead fitting for collection.

The photobioreactor formed in the above-example can be implemented in the following way.

A photobioreactor system formed by joining an approximately cylindrical annulus of flexible, visible-light transmitting, plastic sheet with rigid endcaps at each end of the annulus to form a closed chamber, further comprising a. a plurality of openings within one or more of the endcaps for inlet and outlet tubes;

b. a lower part of the chamber which comprises an aqueous growth medium comprising a culture of genetically enhanced organisms disposed in the growth medium, wherein said organisms are selected from the group consisting of algae and cyanobacteria, and wherein said organisms produce ethanol on a continued daily basis which enters the growth medium;

c. an upper part of the chamber, comprising a headspace above the aqueous growth medium, wherein the headspace comprises carbon dioxide;

d. an inner surface on the upper part of the chamber upon which the ethanol formed by said organisms condenses; and e. a plurality of troughs for the collection of the condensed ethanol In other embodiments, the closing of the ends of the cylindrical annulus can be accomplished without the use of rigid endcaps.

| Photobioreactor Apparatus # 5 | | | | Photobioreactor Apparatus # 6 | | | |
|---|---|---|---|---|---|---|---|
| Sample Date | Sample Time | Sample Type | Ethanol (mM) | Sample Date | Sample Time | Sample Type | Ethanol (mM) |
| Day 1 | 9:00 AM | Photobioreactor | 222.04 | Day 1 | 9:00 AM | Photobioreactor | 230.84 |
| Day 1 | 9:00 AM | Condensate | 279.23 | Day 1 | 9:00 AM | Condensate | 289.87 |
| Day 2 | 9:30 AM | Photobioreactor | 224.99 | Day 2 | 9:30 AM | Photobioreactor | 231.89 |
| Day 2 | 9:30 AM | Condensate | 275.83 | Day 2 | 9:30 AM | Condensate | 292.67 |
| Day 3 | 9:00 AM | Photobioreactor | 222.37 | Day 3 | 9:00 AM | Photobioreactor | 227.12 |
| Day 3 | 9:00 AM | Condensate | 254.80 | Day 3 | 9:00 AM | Condensate | 267.81 |
| Day 6 | 10:00 AM | Photobioreactor | 221.61 | Day 6 | 10:00 AM | Photobioreactor | 228.27 |
| Day 6 | 10:00 AM | Condensate | 256.30 | Day 6 | 10:00 AM | Condensate | 270.83 |
| Day 7 | 9:00 AM | Photobioreactor | 215.26 | Day 7 | 9:00 AM | Photobioreactor | 225.92 |
| Day 7 | 9:00 AM | Condensate | 273.83 | Day 7 | 9:00 AM | Condensate | 273.39 |
| Day 8 | 9:00 AM | Photobioreactor | 212.93 | Day 8 | 9:00 AM | Photobioreactor | 229.38 |
| Day 8 | 9:00 AM | Condensate | 247.37 | Day 8 | 9:00 AM | Condensate | 273.83 |
| Day 9 | 9:00 AM | Photobioreactor | 216.86 | Day 9 | 9:00 AM | Photobioreactor | 232.04 |
| Day 9 | 9:00 AM | Condensate | 253.06 | Day 9 | 9:00 AM | Condensate | 280.41 |
| Day 10 | 9:00 AM | Photobioreactor | 210.78 | Day 10 | 9:00 AM | Photobioreactor | 233.75 |
| Day 10 | 9:00 AM | Condensate | 253.93 | Day 10 | 9:00 AM | Condensate | 272.41 |

We claim:

1. A photobioreactor system formed by joining an approximately cylindrical annulus of flexible, visible-light transmitting, plastic sheet to form a closed chamber, further comprising a. a plurality of openings formed in the chamber for inlet and outlet tubes; b. a lower part of the chamber which comprises an aqueous growth medium comprising a culture of genetically enhanced organisms disposed in the growth medium, wherein said organisms are selected from the group consisting of algae and cyanobacteria, and wherein said organisms produce ethanol on a continued daily basis which enters the growth medium; c. an upper part of the chamber, comprising a headspace above the aqueous growth medium, wherein the headspace comprises carbon dioxide; d. an inner surface on the upper part of the chamber upon which the ethanol formed by said organisms condenses; and e. a plurality of troughs for the collection of the condensed ethanol, wherein the troughs are supported by a flotation device in contact with the aqueous growth medium.

2. The photobioreactor system of claim 1, wherein the troughs are formed from the flexible light transmitting plastic sheet.

3. The photobioreactor system of claim 1, wherein the troughs are formed from the flexible light transmitting plastic sheet, wherein said troughs are supported by air added to the void formed in the construction of each trough to serve as the flotation device in contact with the aqueous growth medium.

\* \* \* \* \*